United States Patent [19]

Jones et al.

[11] Patent Number: 4,551,459

[45] Date of Patent: Nov. 5, 1985

[54] METHOD OF TREATING HEART FAILURE USING (2-OXO-1,2,3,5-TETRAHYDROIMIDAZO-[2,1-B]QUINAZOLINYL)OXYALKYLAMIDES

[75] Inventors: Gordon H. Jones, Cupertino; Michael C. Venuti, San Francisco; Robert Alvarez, Menlo Park; John J. Bruno, Redwood City, all of Calif.

[73] Assignee: Syntex (U.S.A.) Inc., Palo Alto, Calif.

[21] Appl. No.: 599,858

[22] Filed: Apr. 13, 1984

Related U.S. Application Data

[63] Continuation-in-part of Ser. No. 467,125, Feb. 16, 1983, Pat. No. 4,490,371.

[51] Int. Cl.$^4$ .................. A61K 31/505; A61K 27/00
[52] U.S. Cl. .................................. 514/267; 514/234; 514/236
[58] Field of Search .......................... 424/248.54, 251

[56] References Cited

U.S. PATENT DOCUMENTS

| | | | |
|---|---|---|---|
| 3,932,407 | 1/1976 | Bevering et al. | 544/250 |
| 4,070,470 | 1/1978 | Nakagawa et al. | 424/258 |
| 4,256,748 | 3/1981 | Chodnekar et al. | 424/251 |
| 4,313,947 | 2/1982 | Nakagawa et al. | 424/248.54 |

FOREIGN PATENT DOCUMENTS 2001638  2/1979  United Kingdom ............... 424/251

Primary Examiner—Douglas W. Robinson
Attorney, Agent, or Firm—James M. Kanagy; Tom M. Moran

[57] ABSTRACT

Compounds according to the formula

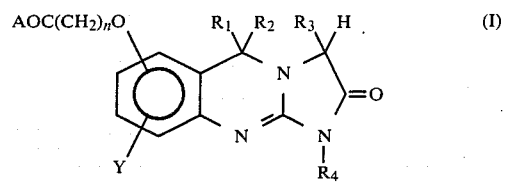

and the pharmaceutically acceptable acid addition salts thereof wherein:

n is an integer of 1 to 6;
$R_1$ is hydrogen or alkyl of 1 to 4 carbon;
$R_2$ is hydrogen or $R_1$ and $R_2$ combined are oxo;
$R_3$ is hydrogen, alkyl of 1 to 6 carbons, phenyl, benzyl, hydroxy lower alkyl and its acylates, carbamoyl alkyl, carboxyalkyl, alkoxycarbonylalkyl or amino acid side chains;
$R_4$ is hydrogen, alkyl of 1 to 6 carbons, benzyl, or hydroxy lower alkyl;
Y is hydrogen, alkyl of 1 to 4 carbon atoms, halo or lower alkoxy;
A is an amide forming group wherein the nitrogen substituents are: hydrogen; alkyl of 1 to 6 carbon atoms; hydroxyalkyl of 1 to 6 carbon atoms and its aliphatic acylates of 1 to 6 carbon atoms or aryl acylates of 7 to 12 carbon atoms; cycloalkyl of 3 to 8 carbon atoms or cycloalkyl lower alkyl of 4 to 12 carbon atoms wherein the cycloalkyl ring is unsubstituted or substituted with a lower alkyl, lower alkoxy, —OH, —OCOR$_5$, halo, —NH$_2$, —N(R$_5$)$_2$, —NHCOR$_5$, —COOH, or —COO(R$_5$) group wherein R$_5$ is lower alkyl; phenyl or phenyl lower alkyl wherein phenyl is unsubstituted or substituted with 1 or more lower alkyl, halo or lower alkoxy groups or an —NH$_2$, —N(R$_5$)$_2$, —NHCOR$_5$, —COOH, or —COOR$_5$ group wherein R$_5$ is lower alkyl; morpholinyl; piperidinyl; perhexylenyl; N-loweralkylpiperazinyl; pyrrolidinyl; tetrahydroquinolinyl; tetrahydroisoquinolinyl; (±)-decahydroquinolinyl or indolinyl. These compounds have inotropic activity.

6 Claims, No Drawings

METHOD OF TREATING HEART FAILURE USING (2-OXO-1,2,3,5-TETRAHYDROIMIDAZO-[2,1-B]QUINAZOLINYL)OXYALKYLAMIDES

The application is a continuation-in-part of now pending U.S. Ser. No. 467,125 filed Feb. 16, 1983 now U.S. Pat. No. 4,490,371, issued on Dec. 25, 1984.

BACKGROUND OF THE INVENTION

1. Field of the Invention

This invention relates to novel substituted 1,2,3,5-tetrahydroimidazo[2,1-b]quinazolines which possess inotropic activity. More specifically the compounds of interest are (2-oxo-1,2,3,5-tetrahydroimidazo[2,1-b]quinazolinyl)oxyalkylamides and their pharmaceutically acceptable acid addition salts.

2. Related Art

Publication of possible interest herein are: F. Kienzle, et al, *Eur. J. Mèd.*, 1982-17, No.6d, pp 547–556 disclosing 1,5-dihydroimidazoquinazolinones as blood platelet aggregation inhibitors; Japanese patent No. 54-163825; and U.S. Pat. No. 3,932,407. These references are relevant primarily for their disclosure of similarly acting compounds, not because the compounds therein are structural analogues to the compounds herein.

SUMMARY OF THE INVENTION

In a first aspect this invention relates to a method of treating heart failure by stimulating suppressed heart activity which occurs during heart failure which method comprises administering a therapeutically effective amount of a compound of formula I alone or in admixture with a pharmaceutically acceptable excipient wherein formula I is represented by the formula

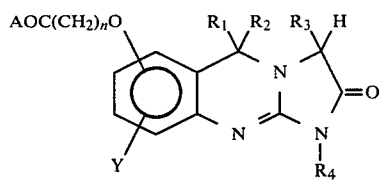

and the pharmaceutically acceptable acid addition salts thereof wherein n is an integer of 1 to 6;

$R_1$ is hydrogen or alkyl of 1 to 4 carbon;

$R_2$ is hydrogen or $R_1$ and $R_2$ combined are oxo;

$R_3$ is hydrogen, alkyl of 1 to 6 carbons, phenyl, benzyl, hydroxy lower alkyl and its acylates, carbamoyl alkyl, carboxyalkyl, alkoxycarbonylalkyl or amino acid side chains;

$R_4$ is hydrogen, alkyl of 1 to 6 carbons, benzyl, or hydroxy lower alkyl;

Y is hydrogen, alkyl of 1 to 4 carbon atoms, halo or lower alkoxy;

A is an amide forming group wherein the nitrogen substituents are: hydrogen; alkyl of 1 to 6 carbon atoms; hydroxyalkyl of 1 to 6 carbon atoms and its aliphatic acylates of 1 to 6 carbon atoms or aryl acylates of 7 to 12 carbon atoms; cycloalkyl of 3 to 8 carbon atoms or cycloalkyl lower alkyl of 4 to 12 carbon atoms wherein the cycloalkyl ring is unsubstituted or substituted with a lower alkyl, lower alkoxy, —OH, —OCOR$_5$, halo, —NH$_2$, —N(R$_5$)$_2$, —NHCOR$_5$, —COOH, or —COO(R$_5$) group wherein $R_5$ is lower alkyl; phenyl or phenyl lower alkyl wherein phenyl is unsubstituted or substituted with 1 or more lower alkyl, halo or lower alkoxy groups or an —NH$_2$, —N(R$_5$)$_2$, —NHCOR$_5$, —COOH, or —COOR$_5$ group wherein $R_5$ is lower alkyl; morpholinyl; piperidinyl; perhexylenyl; N-loweralkylpiperazinyl; pyrrolidinyl; tetrahydroquinolinyl; tetrahydroisoquinolinyl; (±)-decahydroquinolinyl or indolinyl.

DETAILED DESCRIPTION OF THE INVENTION

The compounds of the present invention have inotropic activity. They can strengthen myocardial contraction force by which the heart ventricles can pump the blood into the periphery. Consequently, these compounds also are useful in treating myocardial failure.

The compounds of the present invention are numbered as follows:

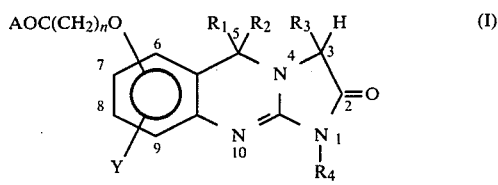

For the purpose of this disclosure, the compounds of the present invention are represented as having the single structural formulation represented by Formula I. However, when $R_4$ is hydrogen compounds of Formula I can exist in several possible tautomeric forms established by the following core structures:

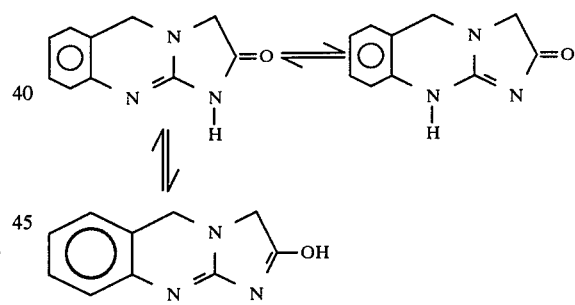

All tautomers are part of the present invention.

The compounds of this invention may be prepared as structural isomers wherein the oxyalkylamide side chain is substituted on the benzene ring at any of the four different available positions. This fact is graphically represented in the generic formula by the drawing of the line into the benzene ring without it being directed to a particular carbon. In addition, the Y substituent or substituents may be present at any of one or more of the remaining ring positions as indicated by Formula I.

Also within the scope of this invention are the optical isomers of those compounds having an asymmetric center, such as when positions 3 and/or 4 of the 1,2,3,5-tetrahydroimidazo[2,1-b]quinazolin-2-one structure are substituted with a substituent other than hydrogen. In addition A may be a substituent which has optical activity such as when A is a cyclic compound, for example, (+)- or (−)-decahydroquinolinyl.

Accordingly, the compounds of the present invention may be prepared either in optically active form or as racemic mixtures. Unless otherwise specified, where appropriate, products of the various synthetic steps described herein will be a racemic mixture. However, the scope of the subject invention herein is not limited to the racemic mixture, but is to encompass the separated individual optical isomers of the disclosed compounds.

If desired, the compounds herein may be resolved into their optical antipodes by conventional resolution means, for example, by separation (e.g. fractional crystallization) of the diastereomeric salts formed by the reaction of these compounds with optically active acids. Exemplary of such optically active acids are the optically active forms of camphor-10-sulfonic acid, 2-bromo-camphor-α-sulfonic acid, camphoric acid, menthoxyacetic acid, tartaric acid, malic acid, diacetyltartaric acid, pyrrolidine-5-carboxylic acid and the like. The separated pure diastereomeric salts may then be cleaved by standard means to afford the respective optical isomers.

For the purpose of this invention, the following phrases should be understood to have the recited meaning.

When reference is made to "alkyl of 1 to 6 carbon atoms" it is meant that there is a branched or unbranched saturated hydrocarbon chain containing, in total, that number of carbon atoms. The phrase refers specifically to such substituents as, for example, methyl, ethyl, n-propyl, i-propyl, n-butyl, tert-butyl, n-pentyl, n-hexyl and the like. The terms "alkyl of 1 to 4 carbon atoms" and "lower alkyl" are used interchangeably and mean methyl, ethyl, n-propyl, i-propyl, n-butyl, t-butyl and the like.

"Lower alkoxy" means the group —OR wherein R is lower alkyl as defined in the foregoing paragraph.

An "hydroxyalkyl" substituent is comprised of 1 to 6 carbon atoms, carbon, hydrogen and one oxygen atom, i.e. an alcohol wherein one terminal carbon atom is substituted on the amide nitrogen and the hydroxyl group is substituted on another carbon, preferably the ω-carbon. Herein the alkyl chain may be straight or branched, preferably straight, is fully saturated and, except for the hydroxyl group, has no other substitution. Examples of hydroxyalkyl substituents are 2-hydroxyethyl, 3-hydroxypropyl, 4-hydroxybutyl, 5-hydroxypentyl and 6-hydroxyhexyl. This is not an exhaustive list of hydroxyalkyl substituents which can be prepared or which can be used in this invention. It is merely intended to exemplify and identify that which is being referred to by the aforementioned phrase.

In the instance where the nitrogen is substituted with an hydroxyalkyl substituent, that hydroxy function can be converted to an ester by reaction with a carboxylic acid. Such an acid may be any unbranched or branched aliphatic acid having 1 to 6 carbon atoms such as, for example, formic acid, acetic acid, propionic acid, butyric acid, pentanoic acid, hexanoic acid or an isomer of these acids which has up to 6 carbon atoms and is fully saturated. These are referred to herein as "aliphatic acylates of 1 to 6 carbon atoms." In addition, the carboxylic acid may be an aryl acid, exemplified by benzoic acid and having up to 7 to 12 carbon atoms. Representative radicals are, in addition to benzoic acid, phenylacetic acid, 3-phenylpropionic acid, 4-phenylbutyric acid, 6-phenylhexanoic acid and the like. Such acids serve to define and exemplify the term "aryl acylates of 7 to 12 carbon atoms."

The phrase "unsubstituted or substituted" is used herein in conjunction with cycloalkyl and aryl substituents to indicate the ring may be have on it only hydrogen or, alternatively, may be substituted one or more of the enumerated radicals as specifically indicated.

"Cycloalkyl of 3 to 8 carbon atoms" refers to a saturated aliphatic ring which contains 3 to 8 carbon atoms and which is substituted directly onto the nitrogen without any intervening methylene groups. Such radicals are, for example, cyclopropyl, cyclobutyl, cyclopentyl, cyclohexyl, cycloheptyl and cyclooctyl.

When reference is made to "cycloaklyl lower alkyl of 4 to 12 carbon atoms" it is meant thereby that the substituents denoted as cycloalkyl of 3 to 8 carbon atoms in the preceding paragraph are attached to the nitrogen by means of a saturated branched or unbranched carbon chain which may have 1 to 4 carbon atoms. Such substituents are, for example, cyclobutylmethyl, 4-cyclobutylbutyl, cyclopentylmethyl, 4-cyclopentylbutyl, cyclohexylmethyl, 4-cyclohexylbutyl, cycloheptylmethyl and 4-cycloheptylbutyl, to name a few examples.

In addition, the cycloalkyl or cycloalkyl lower alkyl radicals recited in the two foregoing paragraphs may be substituted with a radical chosen from the group consisting of lower alkyl, lower alkoxy, —OH, —OCOR$_5$, halo, —NH$_2$, —N(R$_5$)$_2$, —NHCOR$_5$, —COOH, and —COO(R$_5$) group wherein R$_5$ is lower alkyl.

"Phenyl lower alkyl" means a group having at least one and up to four methylene groups with an ω-phenyl group. In this instance the carbon chain is linear, not branched. The phenyl group may be unsubstituted, i.e. contain only hydrogen, or it may be substituted with up to 5 substituents of a single functionality or a combination of the several recited substituents. Examples of unsubstituted phenyl lower alkyl are benzyl, phenethyl, phenylpropyl and phenylbutyl. Examples of substituted phenyl lower alkyl are 4-halophenylalkyl, 2,4-dihalophenylalkyl, 2,4,6-trihalophenylalkyl or 2,3,4,5,6-pentahalo-phenylalkyl wherein halo is as defined below.

In addition the phenyl group may be substituted with one or more lower alkyl groups such as methyl, ethyl, propyl or the like. One or more lower alkoxy groups may also be substituted on the phenyl ring. In addition, phenyl may be substituted with a radical chosen from the group comprised of —NH$_2$, —N(R$_5$)$_2$, —NHCOR$_5$, —COOH, and —COOR$_5$ group wherein R$_5$ is lower alkyl.

The term "halo" refers to fluoro, chloro and bromo and iodo.

The prefix D- and L- are used to describe the individual optical isomers having an asymmetric center at the 3 or 4 position in the 1,2,3,5-tetrahydroimidazo[2,1-b]quinazolin-2-one structure.

Perhexylenyl refers to the substituent dicyclohexyl-2-(2-piperidyl)ethane which is disclosed in British Patent No. 1,025,578.

"Pharmaceutically acceptable acid addition salt" refers to those salts which retain the biological properties and efficacy of the free bases and which are not biologically or otherwise undesirable, formed with inorganic or organic acids. Inorganic acids which may be used are, for example, hydrochloric acid, hydrobromic acid, sulfuric acid, nitric acid, phosphoric acid and the like. Exemplary organic acids are acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicyclic acid and the like.

The compounds of Formula I in free base form may be converted to the acid addition salts by treating the base with a stoichiometric excess of the appropriate organic or inorganic acid. Typically, the free base is dissolved in a polar organic solvent such as ethanol or methanol, and the acid added thereto. The temperature is maintained between about 0° C. and 100° C. The resulting acid addition salt precipitates spontaneously or may be brought out of solution with a less polar solvent.

Administration of the active compounds and salts thereof described herein can be via any of the accepted modes of administration for agents which are cyclic AMP phosphodiesterase inhibitors. These methods include oral, parenteral and otherwise systemic or aerosol forms.

Depending on the intended mode of administration, the compositions used may be in the form of solid, semi-solid or liquid dosage forms, such as, for example, tablets, suppositories, pills, capsules, powders, liquids, suspensions, or the like, preferably in unit dosage forms suitable for single administration of precise dosages. The compositions will include a conventional pharmaceutical carrier or excipient and an active compound of Formula I or the pharmaceutically acceptable salts thereof and, in addition, may include other medicinal agents, pharmaceutical agents, carriers, adjuvants, etc.

For oral administration, a pharmaceutically acceptable non-toxic composition is formed by the incorporation of any of the normally employed excipients, such as, for example pharmaceutical grades of mannitol, lactose, starch, magnesium stearate, sodium saccharin, talcum, cellulose, glucose, sucrose, magnesium, carbonate, and the like. Such compositions take the form of solutions, suspensions, tablets, pills, capsules, powders, sustained release formulations and the like. Such compositions may contain 10%–95% active ingredient, preferably 25–70%.

Parenteral administration is generally characterized by injection, either subcutaneously, intramuscularly or intravenously. Injectables can be prepared in conventional forms, either as liquid solutions or suspensions, solid forms suitable for solution or suspension in liquid prior to injection, or as emulsions. Suitable excipients are, for example, water, saline, dextrose, glycerol, ethanol or the like. In addition, if desired, the pharmaceutical compositions to be administered may also contain minor amounts of non-toxic auxiliary substances such as wetting or emulsifying agents, pH buffering agents and the like, such as for example, sodium acetate, sorbitan monolaurate, triethanolamine oleate, etc.

A more recently devised approach for parenteral administration employs the implantation of a slow-release of sustained-release system, such that a constant level of dosage is maintained. See, e.g., U.S. Pat. Nos. 3,710,795 and 3,773,919.

For systemic administration via suppository, traditional binders and carriers include, e.g. polyalkylene glycols or triglycerides. Such suppositories may be formed from mixtures containing active ingredient in the range of 0.5%–10%; preferably 1–2%.

The amount of active compound administered will of course, be dependent on the subject being treated, the severity of the affliction, the manner of administration, the judgment of the prescribing physician. In any case, a therapeutically effective amount of the drug either alone or in combination with the various excipients listed above or otherwise known will be administered.

Preferred embodiments of the present invention are those compounds wherein n is 3 or 4; $R_1$, $R_2$ are hydorgen and $R_3$ is hydrogen, alkyl of 1 to 6 carbon atoms, hexyl, benxyl, hydroxy lower alkyl and its acylates and carbamoyl alkylates and $R_4$ is hydrogen or methyl, or compounds wherein n is 3 or 4, $R_1$, $R_2$ and $R_4$ are hydrogen, $R_3$ is alkyl of 1 to 6 carbon atoms, phenyl, benzyl, hydroxy lower alkyl and its acylates or carbamoyl alkyl and their optical isomers.

More preferred embodiments are those compounds wherein n is 3 or 4; $R_1$, $R_2$ and $R_3$ are hydrogen; $R_4$ is hydrogen or methyl; and A is an amide wherein the nitrogen is substituted with alkyl of 1 to 6 carbon atoms, hydroxyalkyl of 1 to 6 carbon atoms and its aliphatic acylates of 1 to 6 carbon atoms or aryl acylates of 7 to 12 carbon atoms, cycloalkyl of 3 to 8 carbon atoms, cycloalkyl lower alkyl of 4 to 12 carbon atoms, phenyl or phenyl lower alkyl unsubstituted or substiutued with 1 or more lower alkyl, halo or lower alkoxy groups; perhexylenyl; (±)-decahydroquinolinyl; morpholinyl; piperidinyl; pyrrolindinyl; tetrahydroquinolinyl; tetrahydroisoquinolinyl or indolinyl, or compounds wherein n is 3 or 4, $R_1$, $R_2$ and $R_4$ are hydrogen, $R_3$ is alkyl of 1 to 6 carbon atoms, phenyl, benzyl, hydroxy lower alkyl and its acylates or carbamoyl alkyl and A is an amide wherein the nitrogen is substituted with alkyl of 1 to 6 carbon atoms or cycloalkyl of 3 to 8 carbon atoms and their optical isomers.

Most preferred are the following compounds:
N-cyclohexyl-N-methyl-4-(2-oxo-1,2,3,5-tetrahydroimidazo[2,1-b]quinazolin-7-yl)oxybutyramide;
N-cyclohexyl-N-methyl-4-(2-oxo-L-methyl-1,2,3,5-tetrahydroimidazo[2,1-b]quinazolin-7-yl)oxybutyramide; and
N-cyclohexyl-N-methyl-4-(2-oxo-D-methyl-1,2,3,5-tetrahydroimidazo[2,1-b]quinazolin-7-yl)oxybutyramide.

PREPARATION AND EXAMPLES

Compounds of the present invention can be made by several methods. In this disclosure, the process for preparing the claimed compounds begins with a hydroxy-2-nitrobenzaldehyde which is reacted with an ω-haloalkylester which serves to introduce the alkyl side chain onto the benzene ring. The ester is then hydrolyzed, converted to the acid chloride and treated with the appropriate secondary amine to form the amide. If $R_1$ is to be a group other than hydrogen, that group is introduced into the compound at this point by treating the amide with an appropriate Grignard reagent, which reacts with the aldehyde function, and then oxidizing the resulting alcohol to the ketone. The aldehyde or ketone-containing amide is then treated with an α-amino acid or a salt thereof followed by a cyclization step employing a halo cyanogen and base. Acid addition salts, etc are prepared from this base as needed or desired.

Compounds of the present invention are prepared by the reaction sequence outlined in the following Reaction Schemes.

REACTION SCHEME A

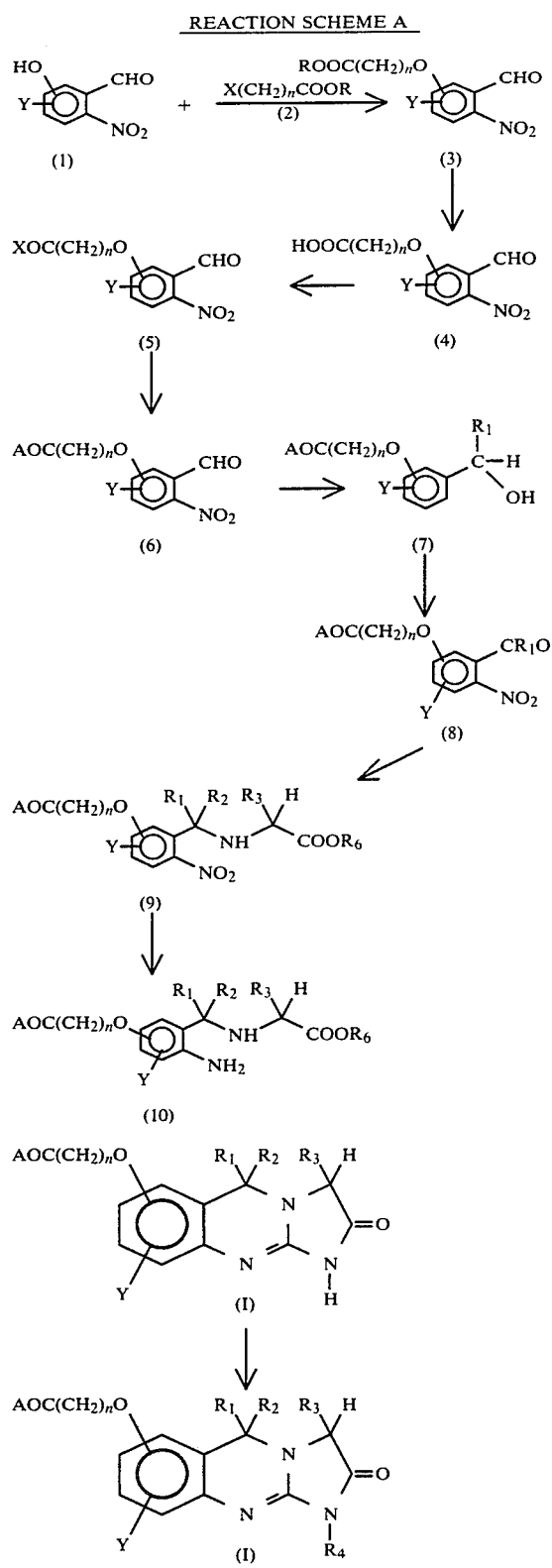

In Reaction Scheme A, the phenols of Formula (1) are known in the art and a number of them are readily available from commercial sources such as Aldrich Chemical Co., Milwaukee, Wis. They are converted to the ω-(formylnitrophenyl)oxyalkyl esters by treating the phenol with an ω-halo substituted alkyl ester of Formula (2). Generally, the reaction is carried out by mixing a mole equivalent of ω-haloalkylester, or up to a 20% excess thereof, with the parent phenol compound in a dry, dipolar aprotic solvent under an inert atmosphere. Solvents which may be used in this reaction are, for example dimethylformamide, propylene carbonate, ethylene carbonate, diethylcarbonate, dimethylcarbonate, tetrahydrofuran and the like. Dimethylformamide is preferred. Preferably the reaction will be carried out in a predried solvent and will be blanketed under a dry inert atmosphere such as nitrogen.

A molar amount, but up to a 30% excess, of weak base is added to the solution to effect the reaction. This weak base may be, for example, an alkali metal carbonate or the like, preferably potassium carbonate. The reaction requires between about 0.25 and 2 hours at between room temperature and 200° C. Preferably the reaction will be carried out for about 1 hour at about 100° C.

Reaction products are isolated by conventionally known methodologies, preferably by solvent extraction into a compatible organic solvent. The Formula (3) product may be further purified by distillation or other appropriate means.

Conversion of the ester to its corresponding acid involves saponification using well-known conditions and reagents. For example a dilute solution of a strong base such as an alkali metal base is added to an alcoholic solution of the ester in small portions and the reaction is allowed to run for about 10 to 60 minutes at a temperature between 0°–50° C. Alcohols which may be used as the solvent for this reaction are, for example, methanol, ethanol, propanol and isopropanol or the like, though it is preferable to use ethanol. The base may be, for example, sodium hydroxide, potassium hydroxide, or lithium hydroxide and the like, but it is preferable and most convenient to use sodium hydroxide. While the concentration of the added base may range between 1 and 6N it is preferable to begin with a 3N solution and add it to the reaction mixture in a ratio of 1 part base for every 4 parts of alcohol solution. Preferably the reaction is allowed to run for about 30 minutes at room temperature after which the solution is neutralized with a concentrated solution of a strong acid such as hydrochloric acid or the like and the solvent evaporated. The product is then further isolated by organic solvent extraction. Crystallization from an appropriate organic solvent gives Formula (4) type compounds.

The conversion of Formula (4) acids to the acid chloride of Formula (5) is a known reaction. The reaction is carried out in a stirred solution of acid in a non-polar, non-reactive solvent such as benzene or toluene or the like to which has been added a small amount of a dipolar aprotic solvent such as dimethylformamide or the like by the addition of an acid halide forming agent, preferably an acid chloride forming agent such as oxalyl chloride. The acid chloride forming reagent should be present in about a 25 to 75% molar excess, preferably a 50% excess, in order to effect a stoichiometric conversion of the acid to the acid halide.

The reaction is allowed to proceed at a temperature between about 0°–45° C. for a time between about 15 minutes and 2 hours. Preferable reaction conditions are about 20° C. for about 1 hour by which time the suspended acid should be completely dissolved.

Without further isolation, the solvent in which the acid chloride is dissolved is converted to a polar solvent by repetitive evaporation and dissolution of the acid chloride in the new polar solvent. This polar solvent may be, for example, an ether such as tetrahydrofuran or diethylether, preferably tetrahydrofuran and preferably dry.

Conversion of the acid chloride to the amide is carried out using Schotten-Baumann reaction conditions which involves dropwise addition of the acid chloride to a well-stirred, cooled mixture of a secondary amine and a weak base in an aqueous organic solvent wherein the organic solvent is the same as that in which the acid chloride is dissolved. The secondary amine should be present in a molar excess of about 30% while the weak base is preferably present in a molar excess of about 35%.

Weak bases having utility for this reaction are the alkali metal carbonates and the like, but particularly sodium carbonate. During addition of the acid chloride to the amine, the reaction mixture should be maintained at a temperature of about 0° C. When the addition of acid chloride is complete the cooling bath may be removed and the reaction allowed to proceed at between about 10°–45° C., but preferably at room temperature. The reaction is complete in about 15 minutes to 2 hours most generally about 1 hour. Removal of the organic solvent leaves an aqueous solution which is extracted to obtain the amide. After appropriate washing of the organic layer, it is evaporated and the amide crystallized from an appropriate organic solvent or chromatographically purified before crystallization.

An alternative method for preparing amides is to catalyze their formation by means 4-dimethylaminopyridine (DMAP) under anhydrous conditions and an inert atmosphere. The acid chloride, dissolved in a dipolar aprotic solvent, such as ethyl ether, is added to a solution of the amine which is dissolved in a dipolar aprotic solvent containing an additional base, for example a trialkylamine, or the like but preferably triethylamine. The amine will be present in a slight molar excess relative to the acid chloride. The DMAP catalyst is present in the mixture in an amount up to a 10% molar amount relative to the acid chloride. During addition of the acid chloride, the reaction mixture is maintained at a temperature of between −10° to +10° C. The inert atmosphere is preferably provided by the use of dry nitrogen.

When addition of the acid chloride is complete the solution is warmed to between about 15°–35° C., preferably room temperature, and the reaction is allowed to proceed at that temperature for between about 30 minutes and 4 hours, preferably 2 hours.

When $R_1$ is alkyl or phenyl, that moiety may be introduced into the compound by reacting the Formula (6) aldehyde with a Grignard reagent or an alkyl lithium compound and then oxidizing the resulting secondary alcohol to the ketone represented by Formula (8).

Alkyl magnesium halide reagents are readily available or may be easily prepared from the alkyl halide and magnesium, a process well-known in the synthetic arts. Formation of the alcohol is effected by adding the aldehyde to a cooled ethereal solution of Grignard reagent wherein the Grignard reagent is present in a 10% molar excess relative to the aldehyde. After addition of the aldehyde is complete, the reaction is refluxed for about 1 to 4 hours, preferably 2 hours. Degradation of the magnesium halide derivative to obtain the alcohol is carried out by dropwise addition of a mineral acid, for example a 25% sulfuric acid solution. This solution is neutralized with a weak base and the alcohol isolated in preparation for treatment with an oxidizing agent to regenerate the carbonyl group.

The oxidation of Formula (7) type compounds is carried out via some strong oxidizing agent under selected conditions which minimize amide oxidation. There may be used, for example, a chromium trioxide-pyridine complex or the like. Preferably the reaction will be carried out under anhydrous conditions under an inert atmosphere and in a polar organic solvent which is inert to the oxidizing reagent, such as a halogenated hydrocarbon. Reaction temperatures will between about 0° to 100° C. for a period of about 1 to 8 hours. A 10% molar excess of oxidizing agent relative to the alcohol is sufficient to effect the desired oxidation.

Herein a preferred oxidizing reagent is the Collins reagent [J. C. Collins, et al., Tetrahedron Letters, p 3363 (1968)] which employs a chromium trioxide-pyridine complex in a halogenated hydrocarbon solvent system. The reaction is carried out under anhydrous conditions in an inert atmosphere. The preferred organic solvents are for example, methylene chloride, carbon tetrachloride, ethylene chloride, or the like. The inert atmosphere is maintained by the use of a dry inert gas, preferably dry nitrogen. Usually a temperature between about 0° to 50° C. for a period of about 0.5 to 5 hours is generally sufficient to effect the reaction. Most preferably the reaction will be carried out in dry methylene chloride under a dry nitrogen atmosphere for about 1 hour at room temperature.

Formula (6) and Formula (8) compounds may then be converted to compounds of Formula (9) by reacting the aldehyde or ketone with an α-amino acid ester. For the purposes of this invention any lower alkyl ester of a naturally occurring α-amino acids or any synthetic α-amino acid ester may be used in the practice of this invention. Generally, the reaction is carried out at a temperature between about 0°–50° C., preferably ambient temperature. A time of between 1 to 8 hours is sufficient to effect the reaction though 3–4 hours is preferable. The reaction is generally carried out in a polar solvent such as an alcohol, for example, methanol, ethanol, propanol, or the like in which the aldehyde/ketone and the ester are soluble. It is preferable to add a water-scavenging agent such as molecular sieves in order to remove water generated during the reaction process.

Initially, a reaction mixture is prepared which contains the carbonyl compound, about a two-fold molar amount of the α-amino acid ester as an acid addition salt, and the water scavenging agent. To this mixture is added a large molar excess of the α-aminocarboxylic acid ester, about 6–10 fold excess. The solution is generally maintained between about 10° to 30° C. during this addition process. After addition of the ester is complete, there is added a cyanoborohydride reducing agent in a molar amount of about one-half that of the carbonyl compound. The reaction is allowed to proceed at a temperature between about 10° to 30° C., preferably at room temperature for a period of between about 1 to 6 hours, preferably 3 to 4 hours.

While the reaction product may be isolated for characterization, etc., that is not necessary and it is most convenient to simply remove precipitated solids, i.e., the molecular sieves and borate salts, by filtration, evaporate the solvent and to take up the residue in an organic solvent. This solution may then be washed with a base and brine to remove impurities after which the solvent is removed and the resulting residue used directly in the next reaction step.

Reduction of the nitro group is most conveniently carried out by catalytic hydrogenation. This reaction may be accomplished by conventionally known means. As practiced herein, the residue from the previous reaction step is dissolved in an appropriate solvent such as, for example, a simple alcohol such as methanol or ethanol. A transition metal catalyst which will selectively reduce the nitro group to the amine without affecting the amide or the phenyl ring is preferred. A preferred catalyst is a palladium catalyst and most preferably it will be palladium on carbon such as the readily available 10% palladium/carbon catalyst.

A small amount of the palladium/carbon catalyst, i.e., between 0.5 and 1.5 grams, will generally be sufficient to effect the reduction. The alcoholic reaction mixture is placed under hydrogen at room temperature and allowed to proceed till an equivalent of hydrogen has been taken up. Isolation of the hydrogenation product is readily accomplished by filtration to remove the catalyst after which the reaction product may be used directly in the following step.

Cyclization of the amine is achieved by means of a cyanogen halide, preferably the bromide. A 5 to 10% molar excess of cyanogen halide is added to the solution from the previous reaction. The resulting solution is refluxed overnight, preferably about 16 hours.

The resulting reaction mixture is then treated with a solution of a strong base for about to 0.5 to 4 hours at a temperature between 0° and 50° C. Bases which may be used to effect this reaction are preferably alkali metal bases such as sodium hydroxide, potassium hydroxide and the like. They are used at a concentration of between about 1 to 6N, preferably 2N. A molar amount of base equivalent to that of the cyanogen halide employed in the previous step is employed in this final reaction step. Preferably the reaction will be allowed to proceed for about 2 hours at room temperature during which time the product generally will precipitate as a powder. The product, Formula I wherein $R_4$ is hydrogen, can be further isolated and characterized by filtration or centrifugation, followed by drying or by recrystallization from an appropriate organic solvent.

Further transformation of compounds where $R_4=H$ to those where $R_4$ is alkyl, benzyl, etc is accomplished by treating the former with alkylating agents and a strong base, such as potassium tert-butoxide or sodium hydride in a dipolar aprotic solvent such as dimethyl formamide.

Where A in Formula I contains an hydroxylalkyl group, that group can be esterified by treating the compound with an acid anhydride in pyridine.

The optical isomers of Formula (I) wherein $R_3$ is a substituent other than hydrogen can be prepared following the same procedures as described above except while reacting with the carbonyl compound (6) or (8), an optically active α-aminocarboxylic acid ester ($NH_2CHR_3COOR_6$) should be used.

The compounds of Formula I in free base form may be converted to the acid addition salts by treatment with a stoichiometric excess of the appropriate organic or inorganic acid. Typically, the free base is dissolved in a polar organic solvent such as ethanol or methanol, and the acid added thereto. The temperature is maintained between about 0° C. and 100° C. The resulting acid addition salt precipitates spontaneously or may be brought out of solution with a less polar solvent.

The acid addition salts of the compounds of Formula I may be decomposed to the corresponding free base by treatment with a stoichiometric excess of a suitable base, such as potassium carbonate or sodium hydroxide, typically in the presence of aqueous solvent, and at a temperature of between about 0° C. and 100° C. The free base form is isolated by conventional means, such as extraction with an organic solvent.

Salts of the compounds of Formula I may be interchanged by taking advantage of differential solubilities of the salts, volatilities or acidities of the acids, or by treating with the appropriately loaded ion exchange resin. For example, the interchange is effected by the reaction of a salt of the compounds of Formula I with a slight stoichiometric excess of an acid of a lower pKa than the acid component of the starting salt. This conversion is carried out at a temperature between about 0° C. and the boiling point of the solvent.

An alternative route for preparing the compounds of Formula (I) wherein $R_2$–$R_4$ are hydrogen is exemplified by the following reaction scheme.

REACTION SCHEME B

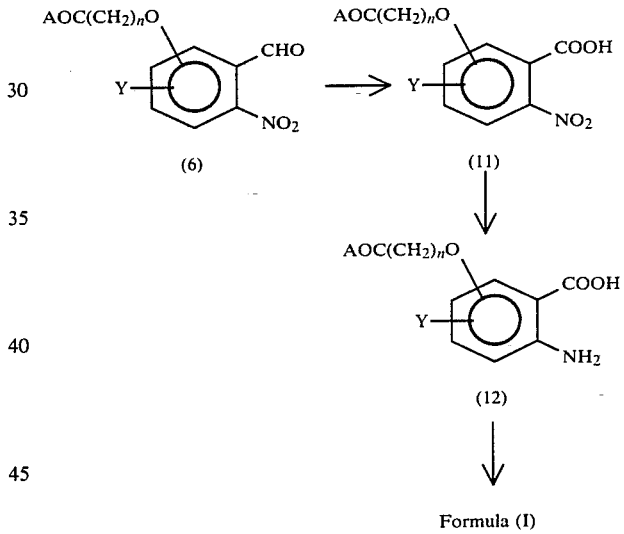

Formula (I)

The compounds of Formula (6) are prepared as described above in Reaction Scheme A.

The compounds of Formula (11) are prepared by oxidizing the corresponding aldehydes with an oxidizing agent such as silver acetate, sodium chloride-sulfamic acid, chromium trioxide-pyridine complexes or alkylammonium permanganates, for example. Usually the reaction will be carried out under an inert atmosphere in a dry, nitrogen-containing solvent at a temperature between about 0°–50° C. for a period of 15 minutes to 3 hours. Preferably the oxidation will be effected by an alkylammonium permanganate such as tetrabutylammonium permanganate in dry pyridine under a dry nitrogen blanket. The reaction is complete in about 1 hour at room temperature.

Reduction of the nitro group to obtain the anthranilic acid compounds of Formula (12) is by catalytic hydrogenation. This reaction employs a heavy metal catalyst dispersed in a simple alcohol containing the nitroacid and put under hydrogen at room temperature until hydrogen uptake is complete. In this instance, it is preferable to add 10% palladium-on-carbon to an ethanolic solution of the nitroacid and place the mixture under about 60 psi hydrogen overnight. Alternatively, the hydrogenation can be carried out with the addition of a mineral acid such as hydrogen chloride, which procedure gives the acid salt directly as a hygroscopic solid.

The amines of Formula (12) are converted directly to Formula I compounds by treating the acids, dissolved in a simple alcohol, with a 2-3 molar excess of 2-methylthiohydantoin. Generally the reaction is carried out under reflux for 1 to 6 hours. Preferably the reaction will be carried out in ethanol under reflux for about 3 hours.

REACTION SCHEME C

Compounds of Formula I may also be prepared from the 7-hydroxy-1,2,3,5-tetrahydroimidazo[2,1-b]quinazolin-2-one or its 6, 8 or 9-hydroxy analogs by the sequence of steps set out below.

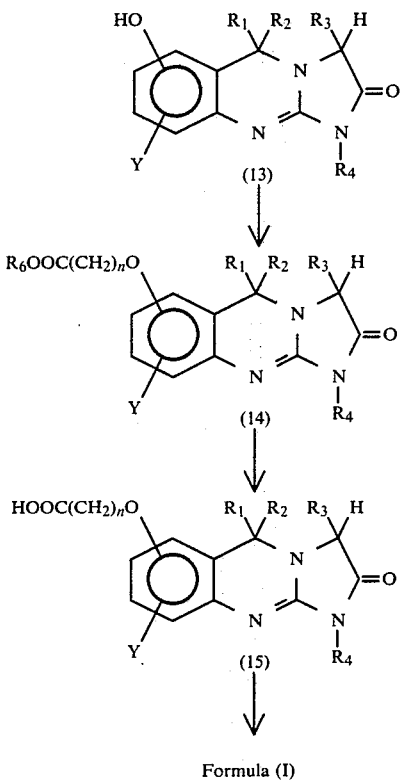

Formula (I)

The compounds of Formula 13 are prepared as described in U.S. Pat. No. 3,932,407 which is incorporated herein by reference.

Alkylation of the hydroxy compounds is achieved by the use of ω-bromoalkanoates (10% molar excess) in a dipolar solvent such dimethylformamide in the same manner described for the preparation of Formula 3 compounds in reaction Scheme A. Ester hydrolysis, to give Formula 14 compounds, is carried out in the same manner as described hereinabove for the conversion of Formula 3 compounds to those of Formula 4 in reaction Scheme A.

Amides are prepared directly from the acid by condensation means. The reaction of the acid and an amide forming agent may be carried out in a dipolar aprotic solvent such as dimethylformamide at a temperature between about 0°–40° C. For example, first the acid and a 10% molar excess of 1-hydroxybenzotriazole is dissolved in the reaction medium after which a dialkylcarbodiimide, preferable diisopropylcarbodiimide is added. After a period of 0.25 to 2 hours, preferably 1 hour, a solution of N-methylcyclohexylamine (20% molar excess) and N-methyl morpholine (20% molar excess) is added. Overnight stirring at about ambient temperature completes the reaction.

The unsubstituted or primary amides of Formula (I) can be prepared by reacting the ester compound (14) with ammonia or other appropriate primary amines either by saturation of a gas or by using 5 equivalents of a liquid in a polar solvent at a temperature of about 100° C.–200° C., sometimes in a pressure vessel.

The following Preparations and Examples are set out to illustrate the reaction steps graphically recited above.

PREPARATION 1

The preparation of ω-((formyl-nitrophenyl)oxy)alkyl acid esters, Formula 3, are described herein.

To a solution of 5-hydroxy-2-nitrobenzaldehyde (84.0 g) and ethyl 4-bromobutyrate (86 ml) in dry dimethylformamide (500 ml) blanketed under dry nitrogen was added potassium carbonate (76.0 g). The reaction mixture was heated to 100° C. for 1 hour. This mixture was cooled, and the solvent removed by evaporation to give a dark brown syrup. This residue was partitioned between ethyl acetate and saturated sodium carbonate (500 ml each). The organic layer was washed with additional saturated sodium carbonate (3×500 ml), and with brine (2×500 ml), dried, filtered and evaporated to give a dark brown syrup. Kugelrohr distillation (180° C., 0.2 mm) afforded ethyl 4-((3-formyl-4-nitrophenyl)oxy)butyrate (95 g) as a bright yellow syrup which slowly darkened upon standing.

Using the above procedure, but substituting the appropriate aldehyde for 5-hydroxy-2-nitrobenzaldehyde and alkyl ω-bromoalkylate for ethyl 4-bromobutyrate there may be prepared, for example, the following compounds:
ethyl 4-(2-chloro-3-formyl-4-nitrophenyl)oxybutyrate;
ethyl 4-(3-formyl-4-nitro-5-chlorophenyl)oxybutyrate;
ethyl 4-(2-chloro-4-nitro-5-formylphenyl)oxybutyrate;
ethyl 4-(3-formyl-4-nitro-5-fluorophenyl)oxybutyrate;
ethyl 4-(2-fluoro-3-formyl-4-nitrophenyl)oxybutyrate;
ethyl 4-(2-methyl-3-formyl-4-nitrophenyl)oxybutyrate;
ethyl 4-(2-formyl-3-nitro-6-fluorophenyl)oxybutyrate;
ethyl 4-(2-formyl-3-nitro-4-chlorophenyl)oxybutyrate;
ethyl 4-(2-formyl-3-nitro-5-fluorophenyl)oxybutyrate;
ethyl 4-(2-formyl-3-nitrophenyl)oxybutyrate;
ethyl 4-(2-formyl-3-nitro-5-methylphenyl)oxybutyrate;
ethyl 4-(2-formyl-3-nitro-6-fluorophenyl)oxybutyrate;
ethyl 4-(2-nitro-3-formylphenyl)oxybutyrate;
ethyl 4-(2-nitro-3-formyl-5-methylphenyl)oxybutyrate;
ethyl 4-(3-nitro-4-formyl-6-fluorophenyl)oxybutyrate;
ethyl 4-(2-chloro-4-formyl-5-nitrophenyl)oxybutyrate;
ethyl 4-(3-nitro-4-formylphenyl)oxybutyrate;
ethyl 4-(3-nitro-4-formyl-5-methylphenyl)oxybutyrate;
ethyl 4-(2-nitro-3-formyl-6-fluorophenyl)oxybutyrate;
ethyl 4-(2-nitro-3-formyl-6-chlorophenyl)oxybutyrate;
ethyl 7-(3-formyl-4-nitrophenyl)oxyheptanoate;
ethyl 7-(2-formyl-3-nitrophenyl)heptanoate;
ethyl 7-(2-chloro-3-formyl-4-nitrophenyl)heptanoate;
ethyl 7-(2-methyl-3-formyl-4-nitrophenyl)heptanoate;
ethyl 7-(3-formyl-4-nitro-5-chlorophenyl)heptanoate;
ethyl 7-(2-formyl-3-nitrophenyl)heptanoate;
ethyl 7-(2-formyl-3-nitro-4-fluorophenyl)heptanoate;

ethyl 7-(2-methyl-3-formyl-4-nitrophenyl)heptanoate;
ethyl 7-(2-formyl-3-nitro-5-chlorophenyl)heptanoate;
ethyl 7-(2-nitro-3-formylphenyl)heptanoate;
ethyl 7-(2-nitro-3-formyl-4-fluorophenyl)heptanoate;
ethyl 7-(2-nitro-3-formyl-6-chlorophenyl)heptanoate;
ethyl 7-(2-nitro-3-formyl-5-methylphenyl)heptanoate;
ethyl 7-(3-nitro-4-formylphenyl)heptanoate;
ethyl 7-(3-nitro-4-formyl-5-methylphenyl)heptanoate;
ethyl 5-(2-formyl-3-nitrophenyl)oxypentanoate;
ethyl 5-(2-formyl-3-nitro-4-chlorophenyl)oxypentanoate;
ethyl 5-(2-formyl-3-nitro-4-methylphenyl)oxypentanoate;
ethyl 5-(2-formyl-3-nitro-6-methylphenyl)oxypentanoate;
ethyl 5-(3-formyl-4-nitro-5-chlorophenyl)oxypentanoate;
ethyl 5-(2-chloro-3-formyl-4-nitrophenyl)oxypentanoate;
ethyl 5-(3-formyl-4-nitrophenyl)oxypentanoate;
ethyl 5-(3-nitro-4-formylphenyl)oxypentanoate;
ethyl 5-(3-nitro-4-formyl-5-methylphenyl)oxypentanoate;
ethyl 5-(3-nitro-4-formyl-6-chlorophenyl)oxypentanoate;
ethyl 5-(3-formyl-4-nitro-6-chlorophenyl)oxypentanoate;
ethyl 5-(2-nitro-3-formylphenyl)oxypentanoate;
ethyl 5-(2-nitro-3-formyl-4-methylphenyl)oxypentanoate;
ethyl 5-(2-nitro-3-formyl-6-chlorophenyl)oxypentanoate;
ethyl 6-(2-formyl-3-nitrophenyl)oxyhexanoate;
ethyl 6-(2-formyl-3-nitro-4-chlorophenyl)oxyhexanoate;
ethyl 6-(2-formyl-3-nitro-6-chlorophenyl)oxyhexanoate;
ethyl 6-(3-formyl-4-nitrophenyl)oxyhexanoate;
ethyl 6-(3-formyl-4-nitro-6-chlorophenyl)oxyhexanoate;
ethyl 6-(3-formyl-4-nitro-5-methylphenyl)oxyhexanoate;
ethyl 6-(2-nitro-3-formylphenyl)oxyhexanoate;
ethyl 6-(2-nitro-3-formyl-6-fluorophenyl)oxyhexanoate;
ethyl 6-(2-nitro-3-formyl-5-methylphenyl)oxyhexanoate;
ethyl 6-(3-nitro-4-formylphenyl)oxyhexanoate;
ethyl 6-(3-nitro-4-formyl-6-methylphenyl)oxyhexanoate;
ethyl 6-(3-nitro-4-formyl-5-chlorophenyl)oxyhexanoate;
ethyl 2-(2-chloro-3-formyl-4-nitrophenyl)oxyacetate;
ethyl 2-(3-formyl-4-nitrophenyl)oxyacetate;
ethyl 2-(3-formyl-4-nitro-5-chlorophenyl)oxyacetate;
ethyl 2-(2-chloro-4-nitro-5-formylphenyl)oxyacetate; and
ethyl 2-(3-formyl-4-nitro-5-fluorophenyl)oxyacetate.

PREPARATION 2

Ester hydrolysis to give the acids of Formula 4 is described herein.

To a solution of ethyl 4-(3-formyl-4-nitrophenyl)oxybutyrate (65 g) in ethanol (400 ml) was added 3N NaOH (100 ml) in small portions. After 30 minutes at room temperature the reaction mixture was acidified with concentrated HCl and the ethanol evaporated. The aqueous residue was extracted with ethyl acetate (4×200 ml). The combined organic layers were washed with brine (2×200 ml), dried over Na₂SO₄, filtered and evaporated to give a light yellow solid. Trituration with ether afforded 4-(3-formyl-4-nitrophenyl)oxybutyric acid (55 g), m.p. 109°–110° C.

Following the above procedure, the esters prepared as per Preparation 1 are converted to the corresponding acid.

PREPARATION 3

Conversion of the acids of Formula 4 in Reaction Scheme A to the acid halide, preferably the chloride, preparatory to forming the amide compounds of Formula 6 was carried out as follows:

To a stirred suspension of 4-(3-formyl-4-nitrophenyl)oxybutyric acid (12.65 g) in benzene (50 ml) and dimethylformamide (0.5 ml) was added oxalyl chloride (4.40 ml) in small portions. When all the acid had been dissolved, the mixture was stirred for an additional 30 minutes. Evaporation of the solvent gave a thick syrup which was redissolved in dry tetrahydrofuran (50 ml) and reevaporated twice. The final residue of crude acid chloride was dissolved in tetrahydrofuran (50 ml) and used without further purification in the next reaction step.

Proceeding in a similar manner, the acids prepared as per Preparation 2 are converted to the corresponding acid chloride.

PREPARATION 4

Preparation of the amides represented by Formula 6 is carried out by either of the following two steps.

A. Into a well-stirred solution of N-methyl-N-cyclohexylamine (29.5 ml) and sodium carbonate (28.8 g) in tetrahydrofuran (250 ml) and water (500 ml) cooled to 0° C. in an ice bath was added the tetrahydrofuran solution of the 4-(3-formyl-5-nitrophenyl)oxybutyric acid chloride from Preparation 3 dropwise. When addition of the acid chloride was completed, the cooling bath was removed and the mixture allowed to stir at room temperature for 1 hour. Most of the tetrahydrofuran was removed by evaporation and the aqueous residue partitioned between ethyl acetate and saturated sodium carbonate (500 ml each). The combined organic layers were washed with additional saturated sodium carbonate (2×20 ml), water (1×100 ml), 1M HCl (2×200 ml) and with brine (2×200 ml) and dried with sodium sulfate. The ethyl acetate was evaporated to give a residue which was crystallized from ethyl acetate to give N-cyclohexyl-N-methyl-4-(3-formyl-4-nitrophenyl)oxybutyramide, (m.p. 98°–100° C.). Alternatively, the extraction residue was chromatographed on silica gel (10% ethyl acetate in dichloromethane as eluant.

B. A tetrahydrofuran solution of 4-(3-formyl-4-nitrophenyl)oxybutyric acid chloride was added dropwise to a solution of N-cyclohexyl-N-methylamine (60 mmol), triethylamine (9.0 ml) and 4-dimethylaminopyridine (0.6 g) in dry tetrahydrofuran (100 ml) blanketed under nitrogen and cooled to 0° C. by an ice bath. When addition of the acid chloride was complete the reaction was stirred at room temperature for 2 hours. After removal of the tetrahydrofuran, the residue was partitioned between ethyl acetate and 1M HCl (300 ml each). The organic layer was then washed with 1M HCl (2×100 ml), saturated sodium carbonate (3×100 ml) and brine (2×100 ml), dried over sodium sulfate filtered and the ethyl acetate flash evaporated. Purification of the residue was carried out as in method A above.

Using either of these procedures and substituting the appropriate secondary amine and acid chloride for those described, there may be prepared the following representative compounds:

N-cyclohexyl-N-hydroxyethyl-4-(3-formyl-4-nitrophenyl)oxybutyramide, m.p. 108°-110° C.;
N-cyclohexylmethyl-N-hydroxyethyl-4-(3-formyl-4-nitrophenyl)oxybutyramide;
N-hexyl-N-methyl-4-(3-formyl-4-nitrophenyl)oxybutyramide;
N,N-dimethyl-4-(3-formyl-4-nitrophenyl)oxybutyramide;
N-ethyl-N-methyl-4-(3-formyl-4-nitrophenyl)oxybutyramide;
M-pentyl-N-methyl-4-(3-formyl-4-nitrophenyl)oxybutyramide;
N-hexyl-N-hydroxyethyl4-(3-formyl-4-nitrophenyl)oxybutyramide;
N,N-dihexyl-4-(3-formyl-4-nitrophenyl)oxybutyramide;
N,N-dipentyl-4-(3-formyl-4-nitrophenyl)oxybutyramide;
N-cyclohexyl-N-6-hydroxyhexyl-4-(3-formyl-4-nitrophenyl)oxybutyramide;
N-cyclohexyl-N-n-hexyl-4-(3-formyl-4-nitrophenyl)oxybutyramide;
N-cyclopentyl-N-methyl-4-(3-formyl-4-nitrophenyl)oxybutyramide;
N-cyclopropylmethyl-N-methyl-4-(3-formyl-4-nitrophenyl)oxybutyramide;
N-cycloheptyl-N-methyl-4-(3-formyl-4-nitrophenyl)oxybutyramide;
N-cyclopentylbutyl-N-methyl-4-(3-formyl-4-nitrophenyl)oxybutyramide;
N-cyclopentylmethyl-N-methyl-4-(3-formyl-4-nitrophenyl)oxybutyramide;
N-cyclopentyl-N-butyl-4-(3-formyl-4-nitrophenyl)oxybutyramide;
N-cyclopentyl-N-hydroxyethyl-4-(3-formyl-4-nitrophenyl)oxybutyramide;
N-cyclopentylmethyl-N-hydroxyethyl-4-(3-formyl-4-nitrophenyl)oxybutyramide;
N-cyclopentylbutyl-N-hydroxyethyl-4-(3-formyl-4-nitrophenyl)oxybutyramide;
N,N-dicyclohexyl-4-(3-formyl-4-nitrophenyl)oxybutyramide, m.p. 107°-108° C.;
N-cyclohexyl-N-4-hydroxy-n-butyl-4-(3-formyl-4-nitro-5-methylphenyl)oxybutyramide;
N-phenyl-N-methyl-4-(3-formyl-4-nitrophenyl)oxybutyramide, m.p. 72°-73° C.;
N-phenyl-N-hexyl-4-(3-formyl-4-nitrophenyl)oxybutyramide;
N-phenyl-N-hydroxymethyl-4-(3-formyl-4-nitrophenyl)oxybutyramide;
N-phenyl-N-6-hydroxyhexyl-4-(3-formyl-4-nitrophenyl)oxybutyramide;
N-cyclohexyl-N-n-butyl-4-(3-formyl-4-nitrophenyl)oxybutyramide;
N-benzyl-N-methyl-4-(3-formyl-4-nitrophenyl)oxybutyramide, syrup;
N,N-dibenzyl-4-(3-formyl-4-nitrophenyl)oxybutyramide, m.p. 76°-77° C.;
N-diphenylmethyl-N-methyl-4-(3-formyl-4-nitrophenyl)oxybutyramide, m.p. 117°-118° C.;
morpholinyl-4-(3-formyl-4-nitrophenyl)oxybutyramide, m.p. 106°-107° C.;
piperidinyl-4-(3-formyl-4-nitrophenyl)oxybutyramide, m.p. 98°-99° C.;
pyrrolidinyl-4-(3-formyl-4-nitrophenyl)oxybutyramide, m.p. 82°-83° C.;
N-methylpiperazinyl-4-(3-formyl-4-nitrophenyl)oxybutyramide;
tetrahydroquinolinyl-4-(3-formyl-4-nitrophenyl)oxybutyramide, m.p. 95°-96° C.;
tetrahydroisoquinolinyl-4-(3-formyl-4-nitrophenyl)oxybutyramide, m.p. 99°-100° C.;
indolinyl-4-(3-formyl-4-nitrophenyl)oxybutyramide, m.p. 155°-156° C.;
(+)-decahydroquinolinyl-4-(3-formyl-4-nitrophenyl)oxybutyramide;
N-cyclohexyl-N-hydroxyethyl-4-(2-formyl-3-nitro-4-chlolophenyl)oxybutyramide;
N-cyclohexyl-N-methyl-4-(2-formyl-3-nitrophenyl)oxybutyramide;
N-cyclohexyl-N-4-hydroxy-n-butyl-4-(2-formyl-3-nitrophenyl)oxybutyramide;
N-cyclohexyl-N-n-hexyl-4-(2-formyl-3-nitrophenyl)oxybutyramide;
N-phenyl-N-methyl-4-(2-formyl-3-nitrophenyl)oxybutyramide;
N-benzyl-N-methyl-4-(2-formyl-3-nitrophenyl)oxybutyramide;
N,N-dibenzyl-4-(2-formyl-3-nitrophenyl)oxybutyramide;
N,N-dicyclohexyl-4-(2-formyl-3-nitrophenyl)oxybutyramide;
(+)-decahydroquinolinyl-4-(2-formyl-3-nitro-4-chlorophenyl)oxybutyramide;
N-cyclohexyl-N-hydroxyethyl-4-(2-nitro-3-formylphenyl)oxybutyramide;
N-phenyl-N-methyl-4-(2-nitro-3-formylphenyl)oxybutyramide;
N-cyclohexyl-N-methyl-4-(2-nitro-3-formylphenyl)oxybutyramide;
N-benzyl-N-methyl-4-(2-nitro-3-formylphenyl)oxybutyramide;
N,N-dibenzyl-4-(2-nitro-3-formylphenyl)oxybutyramide;
N,N-dicyclohexyl-4-(2-nitro-3-formylphenyl)oxybutyramide;
(+)-decahydroquinolinyl-4-(2-nitro-3-formylphenyl)oxybutyramide;
N-diphenylmethyl-N-methyl-4-(2-nitro-3-formylphenyl)oxybutyramide;
N-cyclohexyl-N-hydroxyethyl-4-(3-nitro-4-formylphenyl)oxybutyramide;
N-cyclohexyl-N-methyl-4-(3-nitro-4-formylphenyl)oxybutyramide;
N-phenyl-N-methyl-4-(3-nitro-4-formylphenyl)oxybutyramide;
N-benzyl-N-methyl-4-(3-nitro-4-formylphenyl)oxybutyramide;
N,N-dibenzyl-4-(3-nitro-4-formylphenyl)oxybutyramide;
N,N-dicyclohexyl-4-(3-nitro-4-formylphenyl)oxybutyramide;
(±)-decahydroquinolinyl-4-(3-nitro-4-formylphenyl)oxybutyramide;
N-diphenylmethyl-N-methyl-4-(3-nitro-4-formylphenyl)oxybutyramide;
N-cyclohexyl-N-hydroxyethyl-7-(3-formyl-4-nitrophenyl)oxyheptanamide;
N-cyclohexyl-N-hydroxymethyl-7-(3-formyl-4-nitrophenyl)oxyheptanamide
N-cyclohexyl-N-n-hexyl-(3-formyl-4-nitrophenyl)-7-oxyheptanamide;

N-benzyl-N-methyl-7-(3-formyl-4-nitrophenyl)oxyheptanamide;
N,N-dibenzyl-7-(3-formyl-4-nitrophenyl)oxyheptanamide;
N-diphenylmethyl-N-methyl-7-(3-formyl-4-nitrophenyl)oxyheptanamide;
(±)-decahydroquinolinyl-7-(3-formyl-4-nitrophenyl)oxyheptanamide;
N-cyclohexyl-N-hydroxyethyl-7-(2-formyl-3-nitro-4-chlolophenyl)oxyheptanamide;
N-cyclohexyl-N-methyl-7-(2-formyl-3-nitrophenyl)oxyheptanamide;
N-cyclohexyl-N-4-hydroxy-n-butyl-7-(2-formyl-3-nitrophenyl)oxyheptanamide;
N-phenyl-N-methyl-7-(2-formyl-3-nitrophenyl)oxyheptanamide;
N-benzyl-N-methyl-7-(2-formyl-3-nitrophenyl)oxyheptanamide;
N-cyclohexyl-N-hydroxyethyl-7-(2-nitro-3-formylphenyl)oxyheptanamide;
N-phenyl-N-methyl-7-(2-nitro-3-formylphenyl)oxyheptanamide;
N-cyclohexyl-N-methyl-7-(2-nitro-3-formylphenyl)oxyheptanamide;
N,N-dicyclohexyl-7-(2-nitro-3-formylphenyl)oxyheptanamide;
N-cyclohexyl-N-hydroxyethyl-7-(3-nitro-4-formyl)oxyphenyl)oxyheptanamide;
N-cyclohexyl-N-butyl-7-(3-nitro-4-formylphenyl)oxyheptanamide;
N-benzyl-N-methyl-7-(3-nitro-4-formylphenyl)oxyheptanamide;
N,N-dibenzyl-7-(3-nitro-4-formylphenyl)oxyheptanamide;
(±)-decahydroquinolinyl-7-(3-nitro-4-formylphenyl)oxyheptanamide;
N-cyclohexyl-N-hydroxyethyl-5-(3-formyl-4-nitrophenyl)oxypentanamide;
N-cyclohexyl-N-hydroxymethyl-5-(3-formyl-4-nitrophenyl)oxypentanamide;
N-cyclohexyl-N-methyl-5-(3-formyl-4-nitrophenyl)oxypentanamide;
N-cyclohexyl-N-hexyl-5-(3-formyl-4-nitrophenyl)oxypentanamide;
N-cyclopentyl-N-6-hydroxyhexyl-5-(3-formyl-4-nitrophenyl)oxypentanamide;
N-cyclopentyl-N-hydroxypropyl-5-(3-formyl-4-nitrophenyl)oxypentanamide;
N-cyclopentyl-N-methyl-5-(b 3-formyl-4-nitrophenyl)oxypentanamide;
N-cyclopentyl-N-hexyl-5-(3-formyl-4-nitrophenyl)oxypentanamide;
N-hexyl-N-methyl-5-(3-formyl-4-nitrophenyl)oxypentanamide;
N-methyl-N-methyl-5-(3-formyl-4-nitrophenyl)oxypentanamide;
N,N-dihexyl-5-(3-formyl-4-nitrophenyl)oxypentanamide;
N-phenyl-N-methyl-5-(3-formyl-4-nitrophenyl)oxypentanamide;
N-benzyl-N-methyl-5-(3-formyl-4-nitrophenyl)oxypentanamide;
N-cyclohexyl-N-hydroxyethyl-5-(2-formyl-3-nitro-4-chlolophenyl)oxypentanamide;
N-cyclohexyl-N-methyl-5-(2-formyl-3-nitrophenyl)oxypentanamide;
N-cyclohexyl-N-butyl-5-(2-formyl-3-nitro-phenyl)oxypentanamide;
N-cyclohexyl-N-hydroxyethyl-5-(2-nitro-3-formylphenyl)oxypentanamide;
N-phenyl-N-methyl-5-(2-nitro-3-formylphenyl)oxypentanamide;
N-cyclohexyl-N-methyl-5-(2-nitro-3-formylphenyl)oxypentanamide;
(±)-decahydroquinolinyl-5-(2-nitro-3-formylphenyl)oxypentanamide;
N-diphenylmethyl-N-methyl-5-(2-nitro-3-formylphenyl)oxypentanamide;
N-cyclohexyl-N-hydroxyethyl-5-(3-nitro-4-formylphenyl)oxypentanamide;
N-cyclohexyl-N-methyl-5-(3-nitro-4-formylphenyl)oxypentanamide;
N-phenyl-N-methyl-5-(3-nitro-4-formylphenyl)oxypentanamide;
(±)-decahydroquinolinyl-5-(3-nitro-4-formylphenyl)oxypentanamide;
N-cyclohexyl-N-3-hydroxypropyl-2-(3-formyl-4-nitrophenyl)oxyacetamide;
N-cyclohexyl-N-hydroxypropyl-2-(3-formyl-4-nitrophenyl)oxyacetamide;
N-phenyl-N-hydroxypropyl-2-(3-formyl-4-nitrophenyl)oxyacetamide;
N-cyclohexyl-N-butyl-2-(3-formyl-4-nitrophenyl)oxyacetamide;
(±)-decahydroquinolinyl-2-(3-formyl-4-nitrophenyl)oxyacetamide;
N-cyclohexyl-N-hydroxyethyl-2-(2-formyl-3-nitro-4-chlolophenyl)oxyacetamide;
N-cyclohexyl-N-hydroxymethyl-2-(2-formyl-3-nitrophenyl)oxyacetamide;
N-cyclohexyl-N-propyl-2-(2-formyl-3-nitrophenyl)oxyacetamide;
N-phenyl-N-methyl-2-(2-formyl-3-nitrophenyl)oxyacetamide;
N-benzyl-N-hydroxyethyl-2-(2-formyl-3-nitrophenyl)oxyacetamide;
N-cyclohexyl-N-hydroxyethyl-2-(2-nitro-3-formylphenyl)oxyacetamide;
N-phenyl-N-hydroxyethyl-2-(2-nitro-3-formylphenyl)oxyacetamide;
N-cyclohexyl-N-methyl-2-(2-nitro-3-formylphenyl)oxyacetamide;
N-benzyl-N-methyl-2-(2-nitro-3-formylphenyl)oxyacetamide;
(±)-decahydroquinolinyl-2-(2-nitro-3-formylphenyl)oxyacetamide;
N-cyclopentyl-N-hydroxypropyl-2-(3-nitro-4-formylphenyl)oxyacetamide;
N-cyclohexyl-N-methyl-2-(3-nitro-4-formylphenyl)oxyacetamide;
N-benzyl-N-methyl-2-(3-nitro-4-formylphenyl)oxyacetamide;
N-cyclohexyl-N-hydroxypropyl-6-(3-formyl-4-nitrophenyl)oxyhexanamide;
N-cyclohexyl-N-hydroxypropyl-6-(3-formyl-4-nitrophenyl)oxyhexanamide;
N-phenyl-N-hydroxypropyl-6-(3-formyl-4-nitrophenyl)oxyhexanamide;
N-cyclohexyl-N-butyl-6-(3-formyl-4-nitrophenyl)oxyhexanamide;
(±)-decahydroquinolinyl-6-(3-formyl-4-nitrophenyl)oxyhexanamide;
N-cyclohexyl-N-hydroxyethyl-6-(2-formyl-3-nitro-4-chlolophenyl)oxyhexanamide;
N-cyclohexyl-N-hydroxypropyl-6-(2-formyl-3-nitrophenyl)oxyhexanamide;

N-cyclohexyl-N-propyl-6-(2-formyl-3-nitrophenyl)oxyhexanamide;
N-phenyl-N-methyl-6-(2-formyl-3-nitrophenyl)oxyhexanamide;
N-benzyl-N-hydroxyethyl-6-(2-formyl-3-nitrophenyl)oxyhexanamide;
N-cyclohexyl-N-hydroxyethyl-6-(2-nitro-3-formylphenyl)oxyhexanamide;
N-phenyl-N-hydroxyethyl-6-(2-nitro-3-formylphenyl)oxyhexanamide;
N-cyclohexyl-N-methyl-6-(2-nitro-3-formylphenyl)oxyhexanamide;
N-benzyl-N-methyl-6-(2-nitro-3-formylphenyl)oxyhexanamide;
($\pm$)-decahydroquinolinyl-6-(2-nitro-3-formylphenyl)oxyhexanamide;
N-cyclopentyl-N-hydroxypropyl-6-(3-nitro-4-formylphenyl)oxyhexanamide;
N-cyclohexyl-N-methyl-6-(3-nitro-4-formylphenyl)oxyhexanamide; and
N-benzyl-N-methyl-6-(3-nitro-4-formylphenyl)oxyhexanamide.

PREPARATION 5

Compounds wherein $R_1$ is alkyl are prepared by a two step process the first of which is as followes.

Into a tetrahydrofuran solution of methyl Grignard reagent (120 mmol), either purchased from commercial sources or freshly generated from the corresponding halide and elemental magnesium, was added dropwise a solution of nitroaldehyde (35 g) in tetrahydrofuran (200 ml). The resulting mixture was warmed to reflux for one hour, then cooled and quenched with saturated aqueous ammonium chloride. Evaporation of the tetrahydrofuran followed by extraction with ethyl acetate provided N-cyclohexyl-N-methyl-4-(3-(1-hydroxyethyl)-4-nitrophenyl)oxybutyramide (30 g).

Proceeding in a similar manner, but substituting the the appropriate reagents and an alkylamide whose preparation is described in Preparation 4, there are prepared the following exemplary alcohols:
N-cyclohexyl-N-methyl-4-(3-(1-hydroxyeth-1-yl)-4-nitrophenyl)oxybutyramide;
N-cyclohexyl-N-methyl-4-(3-(1-hydroxybut-1-yl)-4-nitrophenyl)oxybutyramide;
N-cyclohexyl-N-hydroxyethyl-4-(3-(1-hydroxyeth-1-yl)-4-nitrophenyl)oxybutyramide;
N-cyclohexyl-N-methyl-4-(2-(1-hydroxyeth-1-yl)-3-nitrophenyl)oxybutyramide;
N-cyclohexyl-N-hydroxyethyl-4-(2-(1-hydroxyeth-1-yl)-3-nitrophenyl)oxybutyramide;
N-cyclohexyl-N-methyl-4-(2-nitro-3-(1-hydroxyeth-1-yl)phenyl)oxybutyramide;
N-cyclohexyl-N-hyroxyethyl-4-(2-nitro-3-(1-hydroxyeth-1-yl)phenyl)oxybutyramide;
N-cyclohexyl-N-hydroxyethyl-4-(3-(1-hydroxypropyl)-4-nitrophenyl)oxybutyramide;
N-cyclohexyl-N-methyl-(3-(1-hydroxyeth-1-yl)-4-nitrophenyl)oxyheptanamide;
N-cyclohexyl-N-hydroxyethyl-(3-(1-hydroxyeth-1-yl)-4-nitrophenyl)oxyheptanamide;
N-phenyl-N-methyl-(3-(1-hydroxyeth-1-yl)4-nitrophenyl)oxyheptanamide;
N-cyclohexyl-N-methyl-3-(3-(1-hydroxypropyl)-4-nitrophenyl)oxypropanamide;
N-cyclohexyl-N-hydroxyethyl-3-(3-(1-hydroxyeth-1-yl)-4-nitrophenyl)oxypropanamide;
N-cyclopentyl-N-methyl-3-(3-(1-hydroxyeth-1-yl)-4-nitrophenyl)oxypropanamide;
N-cyclohexyl-N-methyl-6-(3-(1-hydroxyeth-1-yl)-4-nitrophenyloxyhexanamide;
N-cyclohexyl-N-hydroxyethyl-6-(3-(1-hydroxypropyl)-4-nitrophenyl)oxyhexanamide;
N-cyclohexyl-N-methyl-5-(3-(1-hydroxyeth-1-yl)-4-nitrophenyl)oxypentanamide; and
N-cyclohexyl-N-hydroxyethyl-5-(3-(1-hydroxyeth-1-yl)-4-nitrophenyl)oxypentanamide.

PREPARATION 6

Oxidation of the secondary alcohols from Preparation 5 is carried out by the following method.

Anhydrous chromium trioxide, 8 g, was added to a stirred solution of 60 ml of dry pyridine in 200 ml of dry dichloromethane and stirred under a dry nitrogen atmosphere at about 20° C. for 15 minutes. A solution of 27 g of N-cyclohexyl-N-hydroxyethyl-4-(3-(1-hydroxyethyl)-4-nitrophenyl)oxybutyramide in 150 ml of dry dichloromethane was added and the reaction mixture stirred for an additional 30 minutes at room temperature. The solution was decanted from the residue and the residue washed with two 100 ml of dry diethyl ether. The organic solutions are combined, washed successively with two 200 ml portions of water and dried over anhydrous sodium sulphate. Evaporation of the solvent under reduced pressure gives a residue which is crystallized from ethyl acetate to give N-cyclohexyl-N-hydroxyethyl-4-[(3-(ethan-1-on)-4-nitrophenyl)oxy]butyramide.

Proceeding in a similiar manner, the secondary alcohols of Preparation 5 may be converted to the corresponding ketone using the above reagents but substituting the appropriate secondary alcohol for N-cyclehexyl-N-methyl-4-(3-(1-hydroxyethyl)-4-nitrophenyl)oxybutyramide. Examples are:
N-cyclohexyl-N-methyl-4-(3-(butan-1-on)-4-nitrophenyl)oxybutyramide;
N-cyclohexyl-N-hydroxyethyl-4-(3-(ethan-1-on)-4-nitrophenyl)oxybutyramide;
N-cyclohexyl-N-methyl-4-(2-ethan-1-on)-3-nitrophenyl)oxybutyramide;
N-cyclohexyl-N-hydroxyethyl-4-(2-ethan-1-on)-3-nitrophenyl)oxybutyramide;
N-cyclohexyl-N-methyl-4-(2-nitro-3-(ethan-1-on)phenyl)oxybutyramide;
N-cyclohexyl-N-hydroxyethyl-4-(2-nitro-3-(ethan-1-on)phenyl)oxybutyramide;
N-cyclohexyl-N-hydroxyethyl-4-(3-(propan-1-on)-4-nitrophenyl)oxybutyramide;
N-cyclohexyl-N-methyl-7-(3-(ethan-1-on)-4-nitrophenyl)oxyheptanamide;
N-cyclohexyl-N-hydroxyethyl-7-(3-(ethan-1-on)-4-nitrophenyl)oxyheptanamide;
N-cyclohexyl-N-hydroxyethyl-7-(3-phenylmethan-2-on)-4-nitrophenyl)oxyheptanamide;
N-phenyl-N-methyl-7-(3-(ethan-1-on)4-nitrophenyl)oxyheptanamide;
N-cyclohexyl-N-methyl-6-(3-(ethan-1-on)-4-nitrophenyl)oxyhexanamide;
N-cyclohexyl-N-hydroxyethyl-6-(3-(propan-1-on)-4-nitrophenyl)oxyhexanamide;
N-cyclohexyl-N-methyl-5-(3-(ethan-1-on)-4-nitrophenyl)oxypentanamide; and
N-cyclohexyl-N-hydroxyethyl-5-(3-(ethan-1-on)-4-nitrophenyl)oxypentanamide.

PREPARATION 7

Preparation of 5-(N-cyclohexyl-N-methyl-4-butyramide)oxy-2-nitrobenzoic acid and analogues as illustrated by Formula (11) in Reaction Scheme B.

To a solution of 5-(N-cyclohexyl)-N-methyl-4-butyramide)oxy-2-nitrobenzaldehyde (3.5 g) in dry pyridine (20 ml) under a blanket of nitrogen was added solid tetra-N-butylammonium permanganate portionwise over 1 hour. The reaction was stirred at room temperature for 1 hour and was then poured into ethyl acetate/6M hydrogen chloride (100 ml each). Solid sodium bisulfite was added to decolorize the solution and the layers were separated. The aqueous layer was added with ethyl acetate (2×50 ml). The combined organic layers were washed with 1M HCl (3×50 ml) and brine (2×50 ml), dried, filtered, and evaporated to give a syrup which foamed at high vacuum from dichloromethane to yield 5-(N-cyclohexyl-N-methyl-4-butyramide)oxy-2-nitrobenzoic acid as an amorphous solid.

Following this procedure, all of the aldehydes of Preparation 4 are converted to the corresponding acid.

PREPARATION 8

Reduction of the nitroacid compounds from Preparation 7 to their anthranilic acid analog is carried out using the following reagents and conditions.

2-nitro-5-(N-cyclohexyl-N-methyl-4-butyramide)oxybenzoic acid (78.7 g) was dissolved in absolute ethanol (750 ml) and hydrogenated at 60 psi over 10% Pd-C (6 g) overnight. The catalyst was removed by filtration through a pad of Celite, and was thoroughly washed with additional ethanol (250 ml). The combined filtrates were thoroughly evaporated to give a thick syrup which crystallized from hexane/dichloromethane to afford 2-amino-5-(N-cyclohexyl-N-methyl-butyramid-4-yl)oxybenzoic acid as a yellow powder, m.p. 175°-176° C.

Proceeding in a similiar manner, but substituting the appropriate nitroacid for 2-amino-5-(N-cyclohexyl-N-methyl-butyramid-4-yl)oxybenzoic acid all the nitroacids prepared as per Preparation 7 may be reduced to the corresponding amine.

PREPARATION 9

Ethyl 4-(7 oxy-1,2,3,5-tetrahydroimadazo[2,1-b]quinazolin-7-yl)oxybutyrate

To a solution of 7-hydroxy-1,2,3,5-tetrahydroimadazo[2,1-b]quinazolin-2-one (2.6 g) made as per U.S. Pat. No. 3,932,407 and ethyl 4-bromobutyrate (1.72 ml) in 100 ml dimethylformamide was added 1.86 g potassium carbonate. The reaction mixture was sealed under a blanket of nitrogen and heated to 100° C. for 4 hours. The reaction mixture was cooled, poured into 100 ml of water, and the resulting precipitate collected by filtration. Recrystallization from dimethylformamide-water gave 3.24 g of ethyl 4-(2-oxo-1,2,3,5-tetrahydroimadazole[2,1-b]quinazolin-7-yl)oxybutyrate, m.p. 243°-244° C.

PREPARATION 10

4-(2-oxo-1,2,3,5-tetrahydroimadazo[2,1-b]quinazolin-7-yl)oxybutyric acid

To a suspension of ethyl 4-(2-oxo-1,2,3,5-tetrahydroimadazo[2,1-b]quinazolin-7-yl)oxybutyrate (65 g) in ethanol (1000 ml) was added 3N NaOH (100 ml) in small portions. After 30 minutes at room temperature the reaction mixture was acidified with concentrated HCl. The resulting thick precipitate was collected by filtration and/or centrifugation and dried to give 4-(2-oxo-1,2,3,5-tetrahydroimadazo[2,1-b]quinazolin-7-yl)oxybutyric acid (m.p.>300° C.) quantitatively.

Esters prepared as per Preparation 9 above all may be converted to their corresponding acid by the foregoing method.

EXAMPLE 1

N-(7-(N-cyclohexyl-N-methylbutyr-amide)oxy-2-aminobenzyl)glycinate

To a solution of N-cyclohexyl-N-methyl-4-(3-formyl-4-nitrophenyl)oxybutyramide (25 mmol), glycine ethyl ester hydrochloride (6.95 g, 50 mmol) and 3 Å molecular seives (5.0 g) in methanol (75 ml) was added glycine ethyl ester (20.6 g, 200 mmol) via syringe. After allowing the solution to stir for 5 minutes at room temperature, sodium cyanoborohydride (0.95 g, 15 mmol) was added in one amount. The reaction mixture was allowed to stir at room temperature for 3-4 hours. The reaction solution was then filtered to remove precipitated solids and molecular seives, and the methanol was removed by evaporation. The residue was dissolved in ethyl acetate (300 ml) and was washed with 2N sodium hydroxide (2×100 ml) in brine (2×100 ml). The organic extract was dried, filtered and evaporated to give a thick syrup. Owing to the instability of the oil toward distillation, the compound ethyl N-(7-(N-cyclohexyl-N-methylbutyramide)oxy-2-aminobenzyl)glycinate, was used directly in the next reaction step.

Using this procedure but substituting the appropriate α-amino acid alkyl ester and alkylamide for the reagents recited above, an α-amino acid ester group is added to the aldehyde or ketone functionality of those compounds prepared according to Preparations 4 and 6.

EXAMPLE 2

Preparation of N,N-disubstituted 4-(2-oxo-1,2,3,5-tetrahydroimidazo[2,1-b]quinazolin-7-yl)oxybutyramide and related compounds.

A. The thick syrupy residue from Example 1 above was dissolved in absolute ethanol (100 ml) and hydrogenated over 10% Pd-C (1.0 g) until uptake of hydrogen ceased, approximately 4 hours. The catalyst was removed by filtration through a pad of Celite, and pad was washed clean with absolute ethanol (50 ml).

B. The combined filtrates from the previous paragraph were treated with cyanogen bromide (3.20 g, 30 mmol), and the resulting solution maintained at a reflux for 16 hours. Upon cooling, the ethanol was removed, and the residue was dissolved in ethanol (100 ml) and treated with 6N sodium hydroxide (5 ml, 30 mmol) and stirred for 2 hours at room temperature. The product precipitated from this mixture as an off-white to tan powder. The powder was further purified by filtration and a water wash and dried, yielding N-cyclohexyl-N-methyl-4-(2-oxo-1,2,3,5-tetrahydroimidazo[2,1-b]quinazolin-7-yl)oxybutyramide, m.p. 243°-244° C.

Proceeding in a like manner but substituting the appropriate compound prepared as per Preparation 7 for ethyl N-[(7-(N-cyclohexyl-N-methylbutyramid-4-yl)oxy)-2-aminobenzyl)methyl]glycinate, there may be prepared the following exemplary compounds of Formula I:

N-cyclohexyl-N-(2-hydroxyethyl)-4-(2-oxo-1,2,3,5-tetrahydroimidazo[2,1-b]quinazolin-7-yl)oxybutyramide, m.p. 185°–186° C.;

N-cyclohexylmethyl-N-(2-hydroxyethyl)-4-(2-oxo-1,2,3,5-tetrahydroimidazo[2,1-b]quinazolin-7-yl)oxybutyramide;

N-phenyl-N-methyl-4-(2-oxo-1,2,3,5-tetrahydroimidazo[2,1-b]quinazolin-7-yl)oxybutyramide, m.p. 223°–224° C.;

N-cyclohexylmethyl-N-(2-hydroxyethyl)-4-(2-oxo-5-methyl-1,2,3,5-tetrahydroimidazo[2,1-b]quinazolin-7-yl)oxybutyramide;

N-phenyl-N-methyl-4-(2-oxo-3-methyl-1,2,3,5-tetrahydroimidazo[2,1-b]quinazolin-7-yl)oxybutyramide;

N-cyclohexyl-N-(2-hydroxyethyl)-4-(2-oxo-6-chloro-1,2,3,5-tetrahydroimidazo[2,1-b]quinazolin-7-yl)oxybutyramide;

N-cyclohexyl-N-(2-morpholinylethyl)-4-(2-oxo-1,2,3,5-tetrahydroimidazo[2,1-b]quinazolin-7-yl)oxybutyramide, m.p. 115°–117° C.;

N-cyclohexyl-N-n-butyl-4-(2-oxo-1,2,3,5-tetrahydroimidazo[2,1-b]quinazolin-7-yl)oxybutyramide, m.p. 170°–172° C.;

N-cycloheptyl-N-methyl-4-(2-oxo-1,2,3,5-tetrahydroimidazo[2,1-b]quinazolin-7-yl)oxybutyramide, m.p. 226°–228° C.;

N-cyclohexyl-N-(2-methoxyethyl)-4-(2-oxo-1,2,3,5-tetrahydroimidazo[2,1-b]quinazolin-7-yl)oxybutyramide, m.p. 186°–187° C.;

N-cyclohexyl-N-(2-hydroxyethyl)-4-(2-oxo-6-methoxy-1,2,3,5-tetrahydroimidazo[2,1-b]quinazolin-7-yl)oxybutyramide;

N-cyclohexylmethyl-N-(2-hydroxyethyl)-4-(2-oxo-3-methyl-6-chloro-1,2,3,5-tetrahydroimidazo[2,1-b]quinazolin-7-yl)oxybutyramide;

N-cyclohexylbutyl-N-(2-hydroxyethyl)-4-(2-oxo-1,2,3,5-tetrahydroimidazo[2,1-b]quinazolin-7-yl)oxybutyramide;

N-cyclohexyl-N-(2-hydroxyethyl)-4-(2-oxo-6-methyl-1,2,3,5-tetrahydroimidazo[2,1-b]quinazolin-7-yl)oxybutyramide;

N-cyclohexyl-N-(6-hydroxyhexyl)-4-(2-oxo-1,2,3,5-tetrahydroimidazo[2,1-b]quinazolin-7-yl)oxybutyramide;

N-cyclohexyl-N-methyl-4-(2-oxo-6-chloro-1,2,3,5-tetrahydroimidazo[2,1-b]quinazolin-7-yl)oxybutyramide;

N-benzyl-N-methyl-4-(2-oxo-1,2,3,5-tetrahydroimidazo[2,1-b]quinazolin-7-yl)oxybutyramide, m.p. 232°–234° C.;

N,N-dibenzyl-4-(2-oxo-1,2,3,5-tetrahydroimidazo[2,1-b]quinazolin-7-yl)oxybutyramide, m.p. 194°–196° C.;

N,N-dicyclohexyl-4-(2-oxo-1,2,3,5-tetrahydroimidazo[2,1-b]quinazolin-7-yl)oxybutyramide, m.p. 242°–244° C.;

morpholinyl-4-(2-oxo-1,2,3,5-tetrahydroimidazo[2,1-b]quinazolin-7-yl)oxybutyramide, m.p. 288°–290° C.;

N-cyclohexylbutyl-N-(2-hydroxyethyl)-4-(2-oxo-1,2,3,5-tetrahydroimidazo[2,1-b]quinazolin-7-yl)oxybutyramide;

piperidinyl-4-(2-oxo-1,2,3,5-tetrahydroimidazo[2,1-b]quinazolin-7-yl)oxybutyramide, m.p. 276°–278° C.;

pyrrolidinyl-4-(2-oxo-1,2,3,5-tetrahydroimidazo[2,1-b]quinazolin-7-yl)oxybutyramide, m.p. 278°–280° C.;

perhexylenyl-4-(2-oxo-1,2,3,5-tetrahydroimidazo[2,1-b]quinazolin-7-yl)oxybutyramide, m.p. 217°–218° C.;

N-cyclooctyl-N-methyl-4-(2-oxo-1,2,3,5-tetrahydroimidazo[2,1-b]quinazolin-7-yl)oxybutyramide, m.p. 234°–235° C.;

N-cyclopentyl-N-methyl-4-(2-oxo-1,2,3,5-tetrahydroimidazo[2,1-b]quinazolin-7-yl)oxybutyramide, m.p. 262°–263° C.;

N-cyclopentyl-N-(2-hydroxyethyl)-4-(2-oxo-6-chloro-1,2,3,5-tetrahydroimidazo[2,1-b]quinazolin-7-yl)oxybutyramide;

N-cyclopentylmethyl-N-(2-hydroxyethyl)-4-(2-oxo-1,2,3,5-tetrahydroimidazo[2,1-b]quinazolin-7-yl)oxybutyramide;

N-cyclohexyl-N-ethyl-4-(2-oxo-1,2,3,5-tetrahydroimidazo[2,1-b]quinazolin-7-yl)oxybutyramide, m.p. 220°–221° C.;

N-cyclohexyl-N-isopropyl-4-(2-oxo-1,2,3,5-tetrahydroimidazo[2,1-b]quinazolin-7-yl)oxybutyramide, m.p. 244°–246° C.;

N-methylpiperazinyl-4-(2-oxo-1,2,3,5-tetrahydroimidazo[2,1-b]quinazolin-7-yl)oxybutyramide;

tetrahydroquinolinyl-4-(2-oxo-1,2,3,5-tetrahydroimidazo[2,1-b]quinazolin-7-yl)oxybutyramide, m.p. 203°–204° C.;

tetrahydroisoquinolinyl-4-(2-oxo-1,2,3,5-tetrahydroimidazo[2,1-b]quinazolin-7-yl)oxybutyramide, m.p. 216°–218° C.;

indolinyl-4-(2-oxo-1,2,3,5-tetrahydroimidazo[2,1-b]quinazolin-7-yl)oxybutyramide, m.p. 264°–266° C.;

(±)-decahydroquinloninyl-4-(2-oxo-1,2,3,5-tetrahydroimidazo[2,1-b]quinazolin-7-yl)oxybutyramide, m.p. 218°–220° C.;

N-diphenylmethyl-N-methyl-4-(2-oxo-1,2,3,5-tetrahydroimidazo[2,1-b]quinazolin-7-yl)oxybutyramide, m.p. 232°–234° C.;

N,N-dimethyl-4-(2-oxo-9-methyl-1,2,3,5-tetrahydroimidazo[2,1-b]quinazolin-7-yl)oxybutyramide;

N-methyl-N-hexyl-4-(2-oxo-1,2,3,5-tetrahydroimidazo[2,1-b]quinazolin-7-yl)oxybutyramide;

N,N-di-n-hexyl-4-(2-oxo-1,2,3,5-tetrahydroimidazo[2,1-b]quinazolin-7-yl)oxybutyramide;

N-methyl-N-hydroxypropyl-4-(2-oxo-1,2,3,5-tetrahydroimidazo[2,1-b]quinazolin-7-yl)oxybutyramide;

N-n-hexyl-N-(2-hydroxyethyl)-4-(2-oxo-1,2,3,5-tetrahydroimidazo[2,1-b]quinazolin-7-yl)oxybutyramide;

N,N-di(2-hydroxyethyl)-4-(2-oxo-1,2,3,5-tetrahydroimidazo[2,1-b]quinazolin-7-yl)oxybutyramide;

N-phenyl-N-(2-hydroxyethyl)-4-(2-oxo-1,2,3,5-tetrahydroimidazo[2,1-b]quinazolin-7-yl)oxybutyramide;

N-phenyl-N-n-hexyl-4-(2-oxo-1,2,3,5-tetrahydroimidazo[2,1-b]quinazolin-7-yl)oxybutyramide;

N-benzyl-N-ethyl-4-(2-oxo-1,2,3,5-tetrahydroimidazo[2,1-b]quinazolin-7-yl)oxybutyramide;

N-benzyl-N-(2-hydroxyethyl)-4-(2-oxo-1,2,3,5-tetrahydroimidazo[2,1-b]quinazolin-7-yl)oxybutyramide;

N-(4-chlorobenzyl)-N-methyl-4-(2-oxo-1,2,3,5-tetrahydroimidazo[2,1-b]quinazolin-7-yl)oxybutyramide;

N-(4-methoxybenzyl)-N-methyl-4-(2-oxo-1,2,3,5-tetrahydroimidazo[2,1-b]quinazolin-7-yl)oxybutyramide;

N-cyclohexyl-N-methyl-4-(2-oxo-1,2,3,5-tetrahydroimidazo[2,1-b]quinazolin-6-yl)oxybutyramide, m.p. 256°–258° C.;

N-cyclohexylbutyl-N-(2-hydroxyethyl)-4-(2-oxo-1,2,3,5-tetrahydroimidazo[2,1-b]quinazolin-6-yl)oxybutyramide;

N-cyclohexylmethyl-N-(2-hydroxyethyl)-4-(2-oxo-1,2,3,5-tetrahydroimidazo[2,1-b]quinazolin-6-yl)oxybutyramide;

N-phenyl-N-methyl-4-(2-oxo-1,2,3,5-tetrahydroimidazo[2,1-b]quinazolin-6-yl)oxybutyramide;
N-cyclohexyl-N-(2-hydroxyethyl)-4-(2-oxo-7-chloro-1,2,3,5-tetrahydroimidazo[2,1-b]quinazolin-6-yl)oxybutyramide;
N-cyclohexyl-N-(2-hydroxyethyl)-4-(2-oxo-7-methyl-1,2,3,5-tetrahydroimidazo[2,1-b]quinazolin-6-yl)oxybutyramide;
N-cyclohexyl-N-methyl-4-(2-oxo-9-chloro-1,2,3,5-tetrahydroimidazo[2,1-b]quinazolin-6-yl)oxybutyramide;
N-benzyl-N-methyl-4-(2-oxo-1,2,3,5-tetrahydroimidazo[2,1-b]-6-oxoquinazolin-6-yl)oxybutyramide;
N-cyclopentyl-N-(2-hydroxyethyl)-4-(2-oxo-1,2,3,5-tetrahydroimidazo[2,1-b]quinazolin-6-yl)oxybutyramide;
N-cyclopentylmethyl-N-(2-hydroxyethyl)-4-(2-oxo-1,2,3,5-tetrahydroimidazo[2,1-b]quinazolin-6-yl)oxybutyramide;
(±)-decahydroquinolinyl-4-(2-oxo-1,2,3,5-tetrahydroimidazo[2,1-b]quinazolin-6-yl)oxybutyramide;
N-diphenylmethyl-N-methyl-4-(2-oxo-1,2,3,5-tetrahydroimidazo[2,1-b]quinazolin-6-yl)oxybutyramide;
N-methyl-N-hydroxypropyl-4-(2-oxo-1,2,3,5-tetrahydroimidazo[2,1-b]quinazolin-6-yl)oxybutyramide;
N-cyclohexyl-N-(6-hydroxyhexyl)-4-(2-oxo-1,2,3,5-tetrahydroimidazo[2,1-b]quinazolin-6-yl)oxybutyramide;
N-phenyl-N-(2-hydroxyethyl)-4-(2-oxo-1,2,3,5-tetrahydroimidazo[2,1-b]quinazolin-6-yl)oxybutyramide;
N-phenyl-N-hexyl-4-(2-oxo-1,2,3,5-tetrahydroimidazo[2,1-b]quinazolin-6-yl)oxybutyramide;
N-(4-chlorobenzyl)-N-(2-hydroxyethyl)-4-(2-oxo-1,2,3,5-tetrahydroimidazo[2,1-b]quinazolin-6-yl)oxybutyramide;
N-(4-methoxybenzyl)-N-methyl-4-(2-oxo-1,2,3,5-tetrahydroimidazo[2,1-b]quinazolin-6-yl)oxybutyramide;
N-cyclohexyl-N-(2-hydroxyethyl)-4-(2-oxo-6-methyl-1,2,3,5-tetrahydroimidazo[2,1-b]quinazolin-8-yl)oxybutyramide;
N-cyclohexyl-N-(2-hydroxyethyl)-4-(2-oxo-1,2,3,5-tetrahydroimidazo[2,1-b]quinazolin-8-yl)oxybutyramide;
N-cyclohexyl-N-(2-hydroxyethyl)-4-(2-oxo-6-methyl-1,2,3,5-tetrahydroimidazo[2,1-b]quinazolin-8-yl)oxybutyramide;
N-cyclohexylmethyl-N-(2-hydroxyethyl)-4-(2-oxo-1,2,3,5-tetrahydroimidazo[2,1-b]quinazolin-8-yl)oxybutyramide;
N-cyclohexyl-N-(2-hydroxyethyl)-4-(2-oxo-6-chloro-1,2,3,5-tetrahydroimidazo[2,1-b]quinazolin-8-yl)oxybutyramide;
N-cyclohexylbutyl-N-(2-hydroxyethyl)-4-(2-oxo-1,2,3,5-tetrahydroimidazo[2,1-b]quinazolin-8-yl)oxybutyramide;
N-cyclohexy-N-methyl-4-(2-oxo-1,2,3,5-tetrahydroimidazo[2,1-b]quinazolin-8-yl)oxybutyramide, m.p. 113°–114° C.;
N-phenyl-N-methyl-4-(2-oxo-1,2,3,5-tetrahydroimidazo[2,1-b]-7-oxoquinazolin-7-yl)oxybutyramide;
N-cyclohexyl-N-(2-hydroxyethyl)-4-(2-oxo-7-chloro-1,2,3,5-tetrahydroimidazo[2,1-b]quinazolin-8-yl)oxybutyramide;
N-cyclohexyl-N-(2-hydroxyethyl)-4-(2-oxo-7-methyl-1,2,3,5-tetrahydroimidazo[2,1-b]quinazolin-8-yl)oxybutyramide;
N-cyclohexyl-N-methyl-4-(2-oxo-9-chloro-1,2,3,5-tetrahydroimidazo[2,1-b]quinazolin-8-yl)oxybutyramide;
N-benzyl-N-methyl-4-(2-oxo-1,2,3,5-tetrahydroimidazo[2,1-b]quinazolin-8-yl)oxybutyramide;
N-cyclopentyl-N-(2-hydroxyethyl)-4-(2-oxo-1,2,3,5-tetrahydroimidazo[2,1-b]quinazolin-8-yl)oxybutyramide;
N-cyclopentylbutyl-N-(2-hydroxyethyl)-4-(2-oxo-1,2,3,5-tetrahydroimidazo[2,1-b]quinazolin-8-yl)oxybutyramide;
(±)-decahydroquinolinyl-4-(2-oxo-1,2,3,5-tetrahydroimidazo[2,1-b]quinazolin-8-yl)oxybutyramide;
N-diphenylmethyl-N-methyl-4-(2-oxo-1,2,3,5-tetrahydroimidazo[2,1-b]quinazolin-8-yl)oxybutyramide;
N-cyclohexyl-N-(6-hydroxyhexyl)-4-(2-oxo-1,2,3,5-tetrahydroimidazo[2,1-b]quinazolin-8-yl)oxybutyramide;
N-phenyl-N-(2-hydroxyethyl)-4-(2-oxo-1,2,3,5-tetrahydroimidazo[2,1-b]quinazolin-8-yl)oxybutyramide;
N-phenyl-N-hexyl-4-(2-oxo-1,2,3,5-tetrahydroimidazo[2,1-b]quinazolin-8-yl)oxybutyramide;
N-(4-chlorobenzyl)-N-(2-hydroxyethyl)-4-(2-oxo-1,2,3,5-tetrahydroimidazo[2,1-b]quinazolin-8-yl)oxybutyramide;
N-(4-methoxybenzyl)-N-ethyl-4-(2-oxo-1,2,3,5-tetrahydroimidazo[2,1-b]quinazolin-8-yl)oxybutyramide;
N-cyclohexyl-N-(6-hydroxyhexyl)-4-(2-oxo-1,2,3,5-tetrahydroimidazo[2,1-b]quinazolin-8-yl)oxybutyramide;
N-cyclohexyl-N-(2-hydroxyethyl)-4-(2-oxo-1,2,3,5-tetrahydroimidazo[2,1-b]quinazolin-9-yl)oxybutyramide;
N-cyclopentyl-N-(2-hydroxyethyl)-4-(2-oxo-1,2,3,5-tetrahydroimidazo[2,1-b]quinazolin-9-yl)oxybutyramide;
N-phenyl-N-methyl-4-(2-oxo-1,2,3,5-tetrahydroimidazo[2,1-b]quinazolin-9-yl)oxybutyramide;
N-cyclohexyl-N-(2-hydroxyethyl)-4-(2-oxo-6-chloro-1,2,3,5-tetrahydroimidazo[2,1-b]quinazolin-9-yl)oxybutyramide;
N-cyclohexylbutyl-N-(2-hydroxyethyl)-4-(2-oxo-1,2,3,5-tetrahydroimidazo[2,1-b]quinazolin-9-yl)oxybutyramide;
N-cyclohexyl-N-methyl-4-(2-oxo-1,2,3,5-tetrahydroimidazo[2,1-b]quinazolin-9-yl)oxybutyramide, m.p. 110°–111° C.;
N-benzyl-N-methyl-4-(2-oxy-1,2,3,5-tetrahydroimidazo[2,1-b]quinazolin-9-yl)oxybutyramide;
N-cyclopentyl-N-(2-hydroxyethyl)-4-(2-oxy-6-methyl-1,2,3,5-tetrahydroimidazo[2,1-b]quinazolin-9-yl)oxybutyramide;
N-diphenylmethyl-N-methyl-4-(2-oxo-1,2,3,5-tetrahydroimidazo[2,1-b]quinazolin-9-yl)oxybutyramide;
N-cyclohexyl-N-(6-hydroxyhexyl)-4-(2-oxo-1,2,3,5-tetrahydroimidazo[2,1-b]quinazolin-9-yl)oxybutyramide;
N-phenyl-N-(2-hydroxyethyl)-4-(2-oxo-1,2,3,5-tetrahydroimidazo[2,1-b]quinazolin-9-yl)oxybutyramide;
N-cyclohexyl-N-(2-hydroxyethyl)-7-(2-oxo-1,2,3,5-tetrahydroimidazo[2,1-b]quinazolin-7-yl)oxyheptanamide;
N-cyclohexylmethyl-N-(2-hydroxyethyl)-7-(2-oxo-1,2,3,5-tetrahydroimidazo[2,1-b]quinazolin-7-yl)oxyheptanamide;

N-phenyl-N-methyl-7-(2-oxo-1,2,3,5-tetrahydroimidazo[2,1-b]quinazolin-7-yl)oxyheptanamide;
N-cyclohexylmethyl-N-(2-hydroxyethyl)-7-(2-oxo-5-methyl-1,2,3,5-tetrahydroimidazo[2,1-b]quinazolin-7-yl)oxyheptanamide;
N-phenyl-N-(2-hydroxyethyl)-7-(2-oxo-3-methyl-1,2,3,5-tetrahydroimidazo[2,1-b]quinazolin-7-yl)oxyheptanamide;
N-cyclohexyl-N-(2-hydroxyethyl)-7-(2-oxo-6-chloro-1,2,3,5-tetrahydroimidazo[2,1-b]quinazolin-7-yl)oxyheptanamide;
N-cyclohexyl-N-(2-hydroxyethyl)-7-(2-oxo-3-methyl-6-chloro-1,2,3,5-tetrahydroimidazo[2,1-b]quinazolin-7-yl)oxyheptanamide;
N-cyclopentylbutyl-N-(2-hydroxyethyl)-7-(2-oxo-1,2,3,5-tetrahydroimidazo[2,1-b]quinazolin-7-yl)oxyheptanamide;
N-cyclohexyl-N-(2-hydroxyethyl)-7-(2-oxo-6-methyl-1,2,3,5-tetrahydroimidazo[2,1-b]quinazolin-7-yl)oxyheptanamide;
N-cyclohexyl-N-methyl-7-(2-oxo-1,2,3,5-tetrahydroimidazo[2,1-b]quinazolin-7-yl)oxyheptanamide, m.p. 148°–150° C.;
N-cyclohexyl-N-(6-hydroxyhexyl)-7-(2-oxo-1,2,3,5-tetrahydroimidazo[2,1-b]quinazolin-7-yl)oxyheptanamide;
N-cyclohexyl-N-methyl-7-(2-oxo-6-chloro-1,2,3,5-tetrahydroimidazo[2,1-b]quinazolin-7-yl)oxyheptanamide;
N-cyclohexyl-N-(2-hydroxyethyl)-7-(2-oxo-6-methoxy-1,2,3,5-tetrahydroimidazo[2,1-b]quinazolin-7-yl)oxyheptanamide;
N-benzyl-N-methyl-7-(2-oxo-1,2,3,5-tetrahydroimidazo[2,1-b]quinazolin-7-yl)oxyheptanamide;
N-cyclohexylbutyl-N-(2-hydroxethyl)-7-(2-oxo-1,2,3,5-tetrahydroimidazo[2,1-b]quinazolin-7-yl)oxyheptanamide;
N-cyclohexyl-N-(2-hydroxyethyl)-7-(2-oxo-6-methoxy-1,2,3,5-tetrahydroimidazo[2,1-b]quinazolin-7-yl)oxyheptanamide;
N-cyclopentyl-N-(2-hydroxyethyl)-7-(2-oxo-6-chloro-1,2,3,5-tetrahydroimidazo[2,1-b]quinazolin-7-yl)oxyheptanamide;
(±)-decahydroquinolinyl-7-(2-oxo-1,2,3,5-tetrahydroimidazo[2,1-b]quinazolin-7-yl)oxyheptanamide;
N-diphenylmethyl-N-methyl-7-(2-oxo-1,2,3,5-tetrahydroimidazo[2,1-b]quinazolin-7-yl)oxyheptanamide;
N-methyl-N-n-hexyl-7-(2-oxo-1,2,3,5-tetrahydroimidazo[2,1-b]quinazolin-7-yl)oxyheptanamide;
N-n-hexyl-N-(2-hydroxyethyl)-7-(2-oxo-1,2,3,5-tetrahydroimidazo[2,1-b]quinazolin-7-yl)oxyheptanamide;
N-phenyl-N-(2-hydroxyethyl)-7-(2-oxo-1,2,3,5-tetrahydroimidazo[2,1-b]quinazolin-7-yl)oxyheptanamide;
N-phenyl-N-n-hexyl-7-(2-oxo-1,2,3,5-tetrahydroimidazo[2,1-b]quinazolin-7-yl)oxyheptanamide;
N-benzyl-N-(2-hydroxyethyl)-7-(2-oxo-1,2,3,5-tetrahydroimidazo[2,1-b]quinazolin-7-yl)oxyheptanamide;
N-(4-chlorobenzyl)-N-methyl-7-(2-oxo-1,2,3,5-tetrahydroimidazo[2,1-b]quinazolin-7-yl)oxyheptanamide;
N-(4-methoxybenzyl)-N-methyl-7-(2-oxo-1,2,3,5-tetrahydroimidazo[2,1-b]quinazolin-7-yl)oxyheptanamide;
N-cyclohexylbutyl-N-(2-hydroxyethyl)-7-(2-oxo-1,2,3,5-tetrahydroimidazo[2,1-b]quinazolin-6-yl)oxyheptanamide;
N-phenyl-N-methyl-7-(2-oxo-1,2,3,5-tetrahydroimidazo[2,1-b]quinazolin-6-yl)oxyheptanamide;
N-cyclohexyl-N-(2-hydroxyethyl)-7-(2-oxo-7-chloro-1,2,3,5-tetrahydroimidazo[2,1-b]quinazolin-6-yl)oxyheptanamide;
N-cyclohexyl-N-(2-hydroxyethyl)-7-(2-oxo-7-methyl-1,2,3,5-tetrahydroimidazo[2,1-b]quinazolin-6-yl)oxyheptanamide;
N-cyclohexyl-N-methyl-7-(2-oxo-9-chloro-1,2,3,5-tetrahydroimidazo[2,1-b]quinazolin-6-yl)oxyheptanamide;
N-benzyl-N-methyl-7-(2-oxo-1,2,3,5-tetrahydroimidazo[2,1-b]quinazolin-6-yl)oxyheptanamide;
N-cyclopentyl-N-(2-hydroxyethyl)-7-(2-oxo-1,2,3,5-tetrahydroimidazo[2,1-b]quinazolin-6-yl)oxyheptanamide;
N-cyclopentylbutyl-N-(2-hydroxyethyl)-7-(2-oxo-1,2,3,5-tetrahydroimidazo[2,1-b]quinazolin-6-yl)oxyheptanamide;
(±)-decahydroquinolinyl-7-(2-oxo-1,2,3,5-tetrahydroimidazo[2,1-b]quinazolin-6-yl)oxyheptanamide;
N-cyclohexyl-N-(6-hydroxyhexyl)-7-(2-oxo-1,2,3,5-tetrahydroimidazo[2,1-b]quinazolin-6-yl)oxyheptanamide;
N-phenyl-N-(2-hydroxyethyl)-7-(2-oxo-1,2,3,5-tetrahydroimidazo[2,1-b]quinazolin-6-yl)oxyheptanamide;
N-phenyl-N-hexyl-7-(2-oxo-1,2,3,5-tetrahydroimidazo[2,1-b]quinazolin-6-yl)oxyheptanamide;
N-(4-chlorobenzyl)-N-(2-hydroxyethyl)-7-(2-oxo-1,2,3,5-tetrahydroimidazo[2,1-b]quinazolin-6-yl)oxyheptanamide;
N-(4-methoxybenzyl)-N-methyl-7-(2-oxo-1,2,3,5-tetrahydroimidazo[2,1-b]quinazolin-6-yl)oxyheptanamide;
N-cyclohexyl-N-(2-hydroxyethyl)-7-(2-oxo-6-methyl-1,2,3,5-tetrahydroimidazo[2,1-b]quinazolin-8-yl)oxyheptanamide;
N-cyclohexyl-N-(2-hydroxyethyl)-7-(2-oxo-1,2,3,5-tetrahydroimidazo[2,1-b]quinazolin-8-yl)oxyheptanamide;
N-cyclohexylbutyl-N-(2-hydroxyethyl)-7-(2-oxo-1,2,3,5-tetrahydroimidazo[2,1-b]quinazolin-8-yl)oxyheptanamide;
N-cyclohexyl-N-(2-hydroxyethyl)-7-(2-oxo-6-chloro-1,2,3,5-tetrahydroimidazo[2,1-b]quinazolin-8-yl)oxyheptanamide;
N-phenyl-N-methyl-7-(2-oxo-1,2,3,5-tetrahydroimidazo[2,1-b]quinazolin-8-yl)oxyheptanamide;
N-cyclohexyl-N-(2-hydroxyethyl)-7-(2-oxo-7-chloro-1,2,3,5-tetrahydroimidazo[2,1-b]quinazolin-8-yl)oxyheptanamide;
N-cyclohexyl-N-(2-hydroxyethyl)-7-(2-oxo-7-methyl-1,2,3,5-tetrahydroimidazo[2,1-b]quinazolin-8-yl)oxyheptanamide;
N-benzyl-N-methyl-7-(2-oxo-1,2,3,5-tetrahydroimidazo[2,1-b]quinazolin-8-yl)oxyheptanamide;
N-cyclopentyl-N-(2-hydroxyethyl)-7-(2-oxo-1,2,3,5-tetrahydroimidazo[2,1-b]quinazolin-8-yl)oxyheptanamide;
N-cyclopentylmethyl-N-methyl-7-(2-oxo-1,2,3,5-tetrahydroimidazo[2,1-b]quinazolin-8-yl)oxyheptanamide;
N-cyclopentylbutyl-N-(2-hydroxyethyl)-7-(2-oxo-1,2,3,5-tetrahydroimidazo[2,1-b]quinazolin-8-yl)oxyheptanamide;
(±)-decahydroquinolinyl-7-(2-oxo-1,2,3,5-tetrahydroimidazo[2,1-b]quinazolin-8-yl)oxyheptanamide;
N-diphenylmethyl-N-methyl-7-(2-oxo-1,2,3,5-tetrahydroimidazo[2,1-b]quinazolin-8-yl)oxyheptanamide;

N-phenyl-N-(2-hydroxyethyl)-7-(2-oxo-1,2,3,5-tetrahydroimidazo[2,1-b]quinazolin-8-yl)oxyheptanamide;

N-phenyl-N-hexyl-7-(2-oxo-1,2,3,5-tetrahydroimidazo[2,1-b]quinazolin-8-yl)oxyheptanamide;

N-(4-chlorobenzyl)-N-(2-hydroxyethyl)-7-(2-oxo-1,2,3,5-tetrahydroimidazo[2,1-b]quinazolin-8-yl)oxyheptanamide;

N-cyclohexyl-N-(6-hydroxyhexyl)-7-(2-oxo-1,2,3,5-tetrahydroimidazo[2,1-b]quinazolin-8-yl)oxyheptanamide;

N-cyclohexyl-N-(2-hydroxyethyl)-7-(2-oxo-1,2,3,5-tetrahydroimidazo[2,1-b]quinazolin-9-yl)oxyheptanamide;

N-cyclopentyl-N-(2-hydroxyethyl)-7-(2-oxo-1,2,3,5-tetrahyroimidazo[2,1-b]quinazolin-9-yl)oxyheptanamide;

N-phenyl-N-methyl-7-(2-oxo-1,2,3,5-tetrahydroimidazo[2,1-b]quinazolin-9-yl)oxyheptanamide;

N-cyclohexylbutyl-N-(2-hydroxyethyl)-7-(2-oxo-1,2,3,5-tetrahydroimidazo[2,1-b]quinazolin-9-yl)oxyheptanamide;

N-cyclohexyl-N-methyl-7-(2-oxo-1,2,3,5-tetrahydroimidazo[2,1-b]quinazolin-9-yl)oxyheptanamide;

N-benzyl-N-methyl-7-(2-oxy-1,2,3,5-tetrahydroimidazo[2,1-b]quinazolin-9-yl)oxyheptanamide;

N-cyclopentyl-N-(2-hydroxyethyl)-7-(2-oxy-6-methyl-1,2,3,5-tetrahydroimidazo[2,1-b]quinazolin-9-yl)oxyheptanamide;

N-cyclohexyl-N-(6-hydroxyhexyl)-7-(2-oxo-1,2,3,5-tetrahydroimidazo[2,1-b]quinazolin-9-yl)oxyheptanamide;

N-phenyl-N-(2-hydroxyethyl)-7-(2-oxo-1,2,3,5-tetrahydroimidazo[2,1-b]quinazolin-9-yl)oxyheptanamide;

(±)-decahydroquinolinyl-N-methyl-7-(2-oxo-1,2,3,5-tetrahydroimidazo[2,1-b]quinazolin-9-yl)oxyheptanamide;

N-cyclohexyl-N-(2-hydroxyethyl)-2-(2-oxo-1,2,3,5-tetrahydroimidazo[2,1-b]quinazolin-7-yl)oxyacetamide;

N-phenyl-N-methyl-2-(2-oxo-1,2,3,5-tetrahydroimidazo[2,1-b]quinazolin-7-yl)oxyacetamide;

N-cyclohexylmethyl-N-(2-hydroxyethyl)-2-(2-oxo-5-methyl-1,2,3,5-tetrahydroimidazo[2,1-b]quinazolin-7-yl)oxyacetamide;

N-phenyl-N-(2-hydroxyethyl)-2-(2-oxo-3-methyl-1,2,3,5-tetrahydroimidazo[2,1-b]quinazolin-7-yl)oxyacetamide;

N-cyclohexyl-N-(2-hydroxyethyl)-2-(2-oxo-6-chloro-1,2,3,5-tetrahydroimidazo[2,1-b]quinazolin-7-yl)oxyacetamide;

N-cyclohexyl-N-methyl-2-(2-oxo-1,2,3,5-tetrahydroimidazo[2,1-b]quinazolin-7-yl)oxyacetamide, m.p. 237°–239° C.;

N-cyclohexyl-N-(2-hydroxyethyl)-2-(2-oxo-3-methyl-6-chloro-1,2,3,5-tetrahydroimidazo[2,1-b]quinazolin-7-yl)oxyacetamide;

N-cyclopentylbutyl-N-(2-hydroxyethyl)-2-(2-oxo-1,2,3,5-tetrahydroimidazo[2,1-b]quinazolin-7-yl)oxyacetamide;

N-cyclohexyl-N-(2-hydroxyethyl)-2-(2-oxo-6-methyl-1,2,3,5-tetrahydroimidazo[2,1-b]quinazolin-7-yl)oxyacetamide;

N-cyclopentyl-N-(2-hydroxyethyl)-2-(2-oxo-6-chloro-1,2,3,5-tetrahydroimidazo[2,1-b]quinazolin-7-yl)oxyacetamide;

(±)-decahydroquinolinyl-2-(2-oxo-1,2,3,5-tetrahydroimidazo[2,1-b]quinazolin-7-yl)oxyacetamide;

N-n-hexyl-N-(2-hydroxyethyl)-2-(2-oxo-1,2,3,5-tetrahydroimidazo[2,1-b]quinazolin-7-yl)oxyacetamide;

N-cyclohexylbutyl-N-(2-hydroxyethyl)-2-(2-oxo-1,2,3,5-tetrahydroimidazo[2,1-b]quinazolin-6-yl)oxyacetamide;

N-phenyl-N-methyl-2-(2-oxo-1,2,3,5-tetrahydroimidazo[2,1-b]quinazolin-6-yl)oxyacetamide;

N-cyclohexyl-N-(2-hydroxyethyl)-2-(2-oxo-7-chloro-1,2,3,5-tetrahydroimidazo[2,1-b]quinazolin-6-yl)oxyacetamide;

N-benzyl-N-methyl-2-(2-oxo-1,2,3,5-tetrahydroimidazo[2,1-b]quinazolin-6-yl)oxyacetamide;

N-cyclopentyl-N-(2-hydroxyethyl)-2-(2-oxo-1,2,3,5-tetrahydroimidazo[2,1-b]quinazolin-6-yl)oxyacetamide;

N-cyclohexyl-N-(2-hydroxyethyl)-2-(2-oxo-1,2,3,5-tetrahydroimidazo[2,1-b]quinazolin-8-yl)oxyacetamide;

N-cyclohexylbutyl-N-(2-hydroxyethyl)-2-(2-oxo-1,2,3,5-tetrahydroimidazo[2,1-b]quinazolin-8-yl)oxyacetamide;

N-phenyl-N-methyl-2-(2-oxo-1,2,3,5-tetrahydroimidazo[2,1-b]quinazolin-8-yl)oxyacetamide;

N-cyclopentyl-N-(2-hydroxyethyl)-2-(2-oxo-1,2,3,5-tetrahydroimidazo[2,1-b]quinazolin-8-yl)oxyacetamide;

N-cyclopentylmethyl-N-methyl-2-(2-oxo-1,2,3,5-tetrahydroimidazo[2,1-b]quinazolin-8-yl)oxyacetamide;

(±)-decahydroquinolinyl-2-(2-oxo-1,2,3,5-tetrahydroimidazo[2,1-b]quinazolin-8-yl)oxyacetamide;

N-cyclohexyl-N-(2-hydroxyethyl)-2-(2oxo-1,2,3,5-tetrahydroimidazo[2,1-b]quinazolin-9-yl)oxyacetamide;

N-cyclopentyl-N-(2-hydroxyethyl)-2-(2-oxo-1,2,3,5-tetrahydroimidazo[2,1-b]quinazolin-9-yl)oxyacetamide;

N-phenyl-N-methyl-2-(2-oxo-1,2,3,5-tetrahydroimidazo[2,1-b]quinazolin-9-yl)oxyacetamide;

N-cyclohexyl-N-methyl-2-(2-oxo-1,2,3,5-tetrahydroimidazo[2,1-b]quinazolin-9-yl)oxyacetamide;

N-benzyl-N-methyl-2-(2-oxo-1,2,3,5-tetrahydroimidazo[2,1-b]quinazolin-9-yl)oxyacetamide;

N-cyclohexyl-N-(6-hydroxyhexyl)-2-(2-oxo-1,2,3,5-tetrahydroimidazo[2,1-b]quinazolin-9-yl)oxyacetamide;

N-cyclohexyl-N-(2-hydroxyethyl)-5-(2-oxo-1,2,3,5-tetrahydroimidazo[2,1-b]quinazolin-7-yl)oxypentanamide;

N-cyclohexylmethyl-N-(2-hydroxyethyl)-5-(2-oxo-1,2,3,5-tetrahydroimidazo[2,1-b]quinazolin-7-yl)oxypentanamide;

N-phenyl-N-methyl-5-(2-oxo-1,2,3,5-tetrahydroimidazo[2,1-b]quinazolin-7-yl)oxypentanamide;

N-cyclohexylmethyl-N-(2-hydroxyethyl)-5-(2-oxo-5-methyl-1,2,3,5-tetrahydroimidazo[2,1-b]quinazolin-7-yl)oxypentanamide;

N-phenyl-N-(2-hydroxyethyl)-5-(2-oxo-3-methyl-1,2,3,5-tetrahydroimidazo[2,1-b]quinazolin-7-yl)oxypentanamide;

N-cyclohexyl-N-(2-hydroxyethyl)-5-(2-oxo-6-chloro-1,2,3,5-tetrahydroimidazo[2,1-b]quinazolin-7-yl)oxypentanamide;

N-cyclohexyl-N-(2-hydroxyethyl)-5-(2-oxo-3-methyl-6-chloro-1,2,3,5-tetrahydroimidazo[2,1-b]quinazolin-7-yl)oxypentanamide;

N-cyclohexyl-N-methyl-5-(2-oxo-1,2,3,5-tetrahydroimidazo[2,1-b]quinazolin-7-yl)oxypentanamide, m.p. 206°–208° C.;

N-cyclopentylbutyl-N-(2-hydroxyethyl)-5-(2-oxo-1,2,3,5-tetrahydroimidazo[2,1-b]quinazolin-7-yl)oxypentanamide;

N-cyclohexyl-N-(2-hydroxyethyl)-5-(2-oxo-6-methyl-1,2,3,5-tetrahydroimidazo[2,1-b]quinazolin-7-yl)oxypentanamide;

N-cyclohexyl-N-(6-hydroxyhexyl)-5-(2-oxo-1,2,3,5-tetrahydroimidazo[2,1-b]quinazolin-7-yl)oxypentanamide;

N-cyclohexyl-N-methyl-5-(2-oxo-6-chloro-1,2,3,5-tetrahydroimidazo[2,1-b]quinazolin-7-yl)oxypentanamide;

N-cyclohexyl-N-(2-hydroxyethyl)-5-(2-oxo-6-methoxy-1,2,3,5-tetrahydroimidazo[2,1-b]quinazolin-7-yl)oxypentanamide;

N-benzyl-N-methyl-5-(2-oxo-1,2,3,5-tetrahydroimidazo[2,1-b]quinazolin-7-yl)oxypentanamide;

N-cyclohexylbutyl-N-(2-hydroxyethyl)-5-(2-oxo-1,2,3,5-tetrahydroimidazo[2,1-b]quinazolin-7-yl)oxypentanamide;

N-cyclohexyl-N-(2-hydroxyethyl)-5-(2-oxo-6-methoxy-1,2,3,5-tetrahydroimidazo[2,1-b]quinazolin-7-yl)oxypentanamide;

N-cyclopentyl-N-(2-hydroxyethyl)-5-(2-oxo-6-chloro-1,2,3,5-tetrahydroimidazo[2,1-b]quinazolin-7-yl)oxypentanamide;

(±)-decahydroquinolinyl-5-(2-oxo-1,2,3,5-tetrahydroimidazo[2,1-b]quinazolin-7-yl)oxypentanamide;

N-diphenylmethyl-N-methyl-5-(2-oxo-1,2,3,5-tetrahydroimidazo[2,1-b]quinazolin-7-yl)oxypentanamide;

N-methyl-N-n-hexyl-5-(2-oxo-1,2,3,5-tetrahydroimidazo[2,1-b]quinazolin-7-yl)oxypentanamide;

N-n-hexyl-N-(2-hydroxyethyl)-5-(2-oxo-1,2,3,5-tetrahydroimidazo[2,1-b]quinazolin-7-yl)oxypentanamide;

N-phenyl-N-(2-hydroxyethyl)-5-(2-oxo-1,2,3,5-tetrahydroimidazo[2,1-b]quinazolin-7-yl)oxypentanamide;

N-phenyl-N-n-hexyl-5-(2-oxo-1,2,3,5-tetrahydroimidazo[2,1-b]quinazolin-7-yl)oxypentanamide;

N-benzyl-N-(2-hydroxyethyl)-5-(2-oxo-1,2,3,5-tetrahydroimidazo[2,1-b]quinazolin-7-yl)oxypentanamide;

N-(4-chlorobenzyl)-N-methyl-5-(2-oxo-1,2,3,5-tetrahydroimidazo[2,1-b]quinazolin-7-yl)oxypentanamide;

N-(4-methoxybenzyl)-N-methyl-5-(2-oxo-1,2,3,5-tetrahydroimidazo[2,1-b]quinazolin-7-yl)oxypentanamide;

N-cyclohexylbutyl-N-(2-hydroxyethyl)-5-(2-oxo-1,2,3,5-tetrahydroimidazo[2,1-b]quinazolin-6-yl)oxypentanamide;

N-phenyl-N-methyl-5-(2-oxo-1,2,3,5-tetrahydroimidazo[2,1-b]quinazolin-6-yl)oxypentanamide;

N-cyclohexyl-N-(2-hydroxyethyl)-5-(2-oxo-7-chloro-1,2,3,5-tetrahydroimidazo[2,1-b]quinazolin-6-yl)oxypentanamide;

N-cyclohexyl-N-(2-hydroxyethyl)-5-(2-oxo-7-methyl-1,2,3,5-tetrahydroimidazo[2,1-b]quinazolin-6-yl)oxypentanamide;

N-cyclohexyl-N-methyl-5-(2-oxo-9-chloro-1,2,3,5-tetrahydroimidazo[2,1-b]quinazolin-6-yl)oxypentanamide;

N-benzyl-N-methyl-5-(2-oxo-1,2,3,5-tetrahydroimidazo[2,1-b]quinazolin-6-yl)oxypentanamide;

N-cyclopentyl-N-(2-hydroxyethyl)-5-(2-oxo-1,2,3,5-tetrahydroimidazo[2,1-b]quinazolin-6-yl)oxypentanamide;

N-cyclopentylbutyl-N-(2-hydroxyethyl)-5-(2-oxo-1,2,3,5-tetrahydroimidazo[2,1-b]quinazolin-6-yl)oxypentanamide;

(±)-decahydroquinolinyl-5-(2-oxo-1,2,3,5-tetrahydroimidazo[2,1-b]quinazolin-6-yl)oxypentanamide;

N-cyclohexyl-N-(6-hydroxyhexyl)-5-(2-oxo-1,2,3,5-tetrahydroimidazo[2,1-b]quinazolin-6-yl)oxypentanamide;

N-phenyl-N-(2-hydroxyethyl)-5-(2-oxo-1,2,3,5-tetrahydroimidazo[2,1-b]quinazolin-6-yl)oxypentanamide;

N-phenyl-N-hexyl-5-(2-oxo-1,2,3,5-tetrahydroimidazo[2,1-b]quinazolin-6-yl)oxypentanamide;

N-(4-chlorobenzyl)-N-(2-hydroxyethyl)-5-(2-oxo-1,2,3,5-tetrahydroimidazo[2,1-b]quinazolin-6-yl)oxypentanamide;

N-(4-methoxybenzyl)-N-methyl-5-(2-oxo-1,2,3,5-tetrahydroimidazo[2,1-b]quinazolin-6-yl)oxypentanamide;

N-cyclohexyl-N-(2-hydroxyethyl)-5-(2-oxo-6-methyl-1,2,3,5-tetrahydroimidazo[2,1-b]quinazolin-8-yl)oxypentanamide;

N-cyclohexyl-N-(2-hydroxyethyl)-5-(2-oxo-1,2,3,5-tetrahydroimidazo[2,1-b]quinazolin-8-yl)oxypentanamide;

N-cyclohexyl-N-(2-hydroxyethyl)-5-(2-oxo-6-methoxy-1,2,3,5-tetrahydroimidazo[2,1-b]quinazolin-8-yl)oxypentanamide;

N-cyclohexylbutyl-N-(2-hydroxyethyl)-5-(2-oxo-1,2,3,5-tetrahydroimidazo[2,1-b]quinazolin-8-yl)oxypentanamide;

N-cyclohexyl-N-(2-hydroxyethyl)-5-(2-oxo-6-chloro-1,2,3,5-tetrahydroimidazo[2,1-b]quinazolin-8-yl)oxypentanamide;

N-phenyl-N-methyl-5-(2-oxo-1,2,3,5-tetrahydroimidazo[2,1-b]quinazolin-8-yl)oxypentanamide;

N-cyclohexyl-N-(2-hydroxyethyl)-5-(2-oxo-7-chloro-1,2,3,5-tetrahydroimidazo[2,1-b]quinazolin-8-yl)oxypentanamide;

N-cyclohexyl-N-(2-hydroxyethyl)-5-(2-oxo-7-methyl-1,2,3,5-tetrahydroimidazo[2,1-b]quinazolin-8-yl)oxypentanamide;

N-benzyl-N-methyl-5-(2-oxo-1,2,3,5-tetrahydroimidazo[2,1-b]quinazolin-8-yl)oxypentanamide;

N-cyclopentyl-N-(2-hydroxyethyl)-5-(2-oxo-1,2,3,5-tetrahydroimidazo[2,1-b]quinazolin-8-yl)oxypentanamide;

N-cyclopentylmethyl-N-methyl-5-(2-oxo-1,2,3,5-tetrahydroimidazo[2,1-b]quinazolin-8-yl)oxypentanamide;

N-cyclopentylbutyl-N-(2-hydroxyethyl)-5-(2-oxo-1,2,3,5-tetrahydroimidazo[2,1-b]quinazolin-8-yl)oxypentanamide;

(±)-decahydroquinolinyl-5-(2-oxo-1,2,3,5-tetrahydroimidazo[2,1-b]quinazolin-8-yl)oxypentanamide;

N-diphenylmethyl-N-methyl-5-(2-oxo-1,2,3,5-tetrahydroimidazo[2,1-b]quinazolin-8-yl)oxypentanamide;

N-phenyl-N-(2-hydroxyethyl)-5-(2-oxo-1,2,3,5-tetrahydroimidazo[2,1-b]quinazolin-8-yl)oxypentanamide;

N-phenyl-N-hexyl-5-(2-oxo-1,2,3,5-tetrahydroimidazo[2,1-b]quinazolin-8-yl)oxypentanamide;

N-(4-chlorobenzyl)-N-(2-hydroxyethyl)-5-(2-oxo-1,2,3,5-tetrahydroimidazo[2,1-b]quinazolin-8-yl)oxypentanamide;

N-cyclohexyl-N-(6-hydroxyhexyl)-5-(2-oxo-1,2,3,5-tetrahydroimidazo[2,1-b]quinazolin-8-yl)oxypentanamide;

N-cyclohexyl-N-(2-hydroxyethyl)-5-(2-oxo-1,2,3,5-tetrahydroimidazo[2,1-b]quinazolin-9-yl)oxypentanamide;

N-cyclopentyl-N-(2-hydroxyethyl)-5-(2-oxo-1,2,3,5-tetrahydroimidazo[2,1-b]quinazolin-9-yl)oxypentanamide;

N-phenyl-N-methyl-5-(2-oxo-1,2,3,5-tetrahydroimidazo[2,1-b]quinazolin-9-yl)oxypentanamide;

N-cyclohexylbutyl-N-(2-hydroxyethyl)-5-(2-oxo-1,2,3,5-tetrahyroimidazo[2,1-b]quinazolin-9-yl)oxypentanamide;

N-cyclohexyl-N-methyl-5-(2-oxo-1,2,3,5-tetrahydroimidazo[2,1-b]quinazolin-9-yl)oxypentanamide;
N-benzyl-N-methyl-5-(2-oxy-1,2,3,5-tetrahydroimidazo[2,1-b]quinazolin-9-yl)oxypentanamide;
N-cyclopentyl-N-(2-hydroxyethyl)-5-(2-oxy-6-methyl-1,2,3,5-tetrahydroimidazo[2,1-b]quinazolin-9-yl)oxypentanamide;
N-cyclohexyl-N-(6-hydroxyhexyl)-5-(2-oxo-1,2,3,5-tetrahydroimidazo[2,1-b]quinazolin-9-yl)oxypentanamide;
N-phenyl-N-(2-hydroxyethyl)-5-(2-oxo-1,2,3,5-tetrahydroimidazo[2,1-b]quinazolin-9-yl)oxypentanamide;
(±)-decahydroquinolinyl-N-methyl-5-(2-oxo-1,2,3,5-tetrahydroimidazo[2,1-b]quinazolin-9-yl)oxypentanamide;
N-cyclohexyl-N-(2-hydroxyethyl)-6-(2-oxo-1,2,3,5-tetrahydroimidazo[2,1-b]quinazolin-7-yl)oxyhexanamide;
N-cyclohexylmethyl-N-(2-hydroxyethyl)-6-(2-oxo-1,2,3,5-tetrahydroimidazo[2,1-b]quinazolin-7-yl)oxyhexanamide;
N-phenyl-N-methyl-6-(2-oxo-1,2,3,5-tetrahydroimidazo[2,1-b]quinazolin-7-yl)oxyhexanamide;
N-cyclohexylmethyl-N-(2-hydroxyethyl)-6-(2-oxo-5-methyl-1,2,3,5-tetrahydroimidazo[2,1-b]quinazolin-7-yl)oxyhexanamide;
N-phenyl-N-(2-hydroxyethyl)-6-(2-oxo-3-methyl-1,2,3,5-tetrahydroimidazo[2,1-b]quinazolin-7-yl)oxyhexanamide;
N-cyclohexyl-N-(2-hydroxyethyl)-6-(2-oxo-6-chloro-1,2,3,5-tetrahydroimidazo[2,1-b]quinazolin-7-yl)oxyhexanamide;
N-cyclohexyl-N-(2-hydroxyethyl)-6-(2-oxo-3-methyl-6-chloro-1,2,3,5-tetrahydroimidazo[2,1-b]quinazolin-7-yl)oxyhexanamide;
N-cyclohexylbutyl-N-(2-hydroxyethyl)-6-(2-oxo-1,2,3,5-tetrahydroimidazo[2,1-b]quinazolin-7-yl)oxyhexanamide;
N-cyclohexyl-N-(2-hydroxyethyl)-6-(2-oxo-6-methyl-1,2,3,5-tetrahydroimidazo[2,1-b]quinazolin-7-yl)oxyhexanamide;
N-cyclohexyl-N-(6-hydroxyhexyl)-6-(2-oxo-1,2,3,5-tetrahydroimidazo[2,1-b]quinazolin-7-yl)oxyhexanamide;
N-cyclohexyl-N-methyl-6-(2-oxo-6-chloro-1,2,3,5-tetrahydroimidazo[2,1-b]quinazolin-7-yl)oxyhexanamide;
N-cyclohexyl-N-(2-hydroxyethyl)-6-(2-oxo-6-methoxy-1,2,3,5-tetrahydroimidazo[2,1-b]quinazolin-7-yl)oxyhexanamide;
N-benzyl-N-methyl-6-(2-oxo-1,2,3,5-tetrahydroimidazo[2,1-b]quinazolin-7-yl)oxyhexanamide;
N-cyclohexylbutyl-N-(2-hydroxyethyl)-6-(2-oxo-1,2,3,5-tetrahydroimidazo[2,1-b]quinazolin-7-yl)oxyhexanamide;
N-cyclohexyl-N-(2-hydroxyethyl)-6-(2-oxo-6-methoxy-1,2,3,5-tetrahydroimidazo[2,1-b]quinazolin-7-yl)oxyhexanamide;
N-cyclohexyl-N-methyl-6-(2-oxo-1,2,3,5-tetrahydroimidazo[2,1-b]quinazolin-7-yl)oxyhexanamide, m.p. 208°–209° C.;
N-cyclohexyl-N-(2-hydroxyethyl)-6-(2-oxo-6-chloro-1,2,3,5-tetrahydroimidazo[2,1-b]quinazolin-7-yl)oxyhexanamide;
(±)-decahydroquinolinyl-6-(2-oxo-1,2,3,5-tetrahydroimidazo[2,1-b]quinazolin-7-yl)oxyhexanamide;
N-diphenylmethyl-N-methyl-6-(2-oxo-1,2,3,5-tetrahydroimidazo[2,1-b]quinazolin-7-yl)oxyhexanamide;
N-methyl-N-n-hexyl-6-(2-oxo-1,2,3,5-tetrahydroimidazo[2,1-b]quinazolin-7-yl)oxyhexanamide;
N-n-hexyl-N-(2-hydroxyethyl)-6-(2-oxo-1,2,3,5-tetrahydroimidazo[2,1-b]quinazolin-7-yl)oxyhexanamide;
N-phenyl-N-(2-hydroxyethyl)-6-(2-oxo-1,2,3,5-tetrahyddroimidazo[2,1-b]quinazolin-7-yl)oxyhexanamide;
N-phenyl-N-n-hexyl-6-(2-oxo-1,2,3,5-tetrahydroimidazo[2,1-b]quinazolin-7-yl)oxyhexanamide;
N-benzyl-N-(2-hydroxyethyl)-6-(2-oxo-1,2,3,5-tetrahydroimidazo[2,1-b]quinazolin-7-yl)oxyhexanamide;
N-(4-chlorobenzyl)-N-methyl-6-(2-oxo-1,2,3,5-tetrahydroimidazo[2,1-b]quinazolin-7-yl)oxyhexanamide;
N-(4-methoxybenzyl)-N-methyl-6-(2-oxo-1,2,3,5-tetrahydroimidazo[2,1-b]quinazolin-7-yl)oxyhexanamide;
N-cyclohexylbutyl-N-(2-hydroxyethyl)-6-(2-oxo-1,2,3,5-tetrahydroimidazo[2,1-b]quinazolin-6-yl)oxyhexanamide;
N-phenyl-N-methyl-6-(2-oxo-1,2,3,5-tetrahydroimidazo[2,1-b]quinazolin-6-yl)oxyhexanamide;
N-cyclohexyl-N-(2-hydroxyethyl)-4-(2-oxo-7-chloro-1,2,3,5-tetrahydroimidazo[2,1-b]quinazolin-6-yl)oxyhexanamide;
N-cyclohexyl-N-(2-hydroxyethyl)-4-(2-oxo-7-methyl-1,2,3,5-tetrahydroimidazo[2,1-b]quinazolin-6-yl)oxyhexanamide;
N-cyclohexyl-N-methyl-6-(2-oxo-9-chloro-1,2,3,5-tetrahydroimidazo[2,1-b]quinazolin-6-yl)oxyhexanamide;
N-benzyl-N-methyl-6-(2-oxo-1,2,3,5-tetrahydroimidazo[2,1-b]quinazolin-6-yl)oxyhexanamide;
N-cyclopentyl-N-(2-hydroxyethyl)-6-(2-oxo-1,2,3,5-tetrahydroimidazo[2,1-b]quinazolin-6-yl)oxyhexanamide;
N-cyclopentylbutyl-N-(2-hydroxyethyl)-6-(2-oxo-1,2,3,5-tetrahydroimidazo[2,1-b]quinazolin-6-yl)oxyhexanamide;
(±)-decahydroquinolinyl-6-(2-oxo-1,2,3,5-tetrahydroimidao[2,1-b]quinazolin-6-yl)oxyhexanamide;
N-cyclohexyl-N-(6-hydroxyhexyl)-6-(2-oxo-1,2,3,5-tetrahydroimidazo[2,1-b]quinazolin-6-yl)oxyhexanamide;
N-phenyl-N-(2-hydroxyethyl)-6-(2-oxo-1,2,3,5-tetrahydroimidazo[2,1-b]quinazolin-6-yl)oxyhexanamide;
N-phenyl-N-hexyl-6-(2-oxo-1,2,3,5-tetrahydroimidazo[2,1-b]quinazolin-6-yl)oxyhexanamide;
N-(4-chlorobenzyl)-N-(2-hydroxyethyl)-6-(2-oxo-1,2,3,5-tetrahydroimidazo[2,1-b]quinazolin-6-yl)oxyhexanamide;
N-(4-methoxybenzyl)-N-methyl-6-(2-oxo-1,2,3,5-tetrahydroimidazo[2,1-b]quinazolin-6-yl)oxyhexanamide;
N-cyclohexyl-N-(2-hydroxyethyl)-6-(2-oxo-6-methyl-1,2,3,5-tetrahydroimidazo[2,1-b]quinazolin-8-yl)oxyhexanamide;
N-cyclohexyl-N-(2-hydroxyethyl)-6-(2-oxo-1,2,3,5-tetrahydroimidazo[2,1-b]quinazolin-8-yl)oxyhexanamide;
N-cyclohexyl-N-(2-hydroxyethyl)-6-(2-oxo-6-methoxy-1,2,3,5-tetrahydroimidazo[2,1-b]quinazolin-8-yl)oxyhexanamide;
N-cyclohexylbutyl-N-(2-hydroxyethyl)-6-(2-oxo-1,2,3,5-tetrahydroimidazo[2,1-b]quinazolin-8-yl)oxyhexanamide;
N-cyclohexyl-N-(2-hydroxyethyl)-6-(2-oxo-6-chloro-1,2,3,5-tetrahydroimidazo[2,1-b]quinazolin-8-yl)oxyhexanamide;

N-phenyl-N-methyl-6-(2-oxo-1,2,3,5-tetrahydroimidazo[2,1-b]quinazolin-8-yl)oxyhexanamide;
N-cyclohexyl-N-(2-hydroxyethyl)-6-(2-oxo-7-chloro-1,2,3,5-tetrahydroimidazo[2,1-b]quinazolin-8-yl)oxyhexanamide;
N-cyclohexyl-N-(2-hydroxyethyl)-6-(2-oxo-7-methyl-1,2,3,5-tetrahydroimidazo[2,1-b]quinazolin-8-yl)oxyhexanamide;
N-benzyl-N-methyl-6-(2-oxo-1,2,3,5-tetrahydroimidazo[2,1-b]quinazolin-8-yl)oxyhexanamide;
N-cyclopentyl-N-(2-hydroxyethyl)-6-(2-oxo-1,2,3,5-tetrahydroimidazo[2,1-b]quinazolin-8-yl)oxyhexanamide;
N-cyclopentylmethyl-N-methyl-6-(2-oxo-1,2,3,5-tetrahydroimidazo[2,1-b]quinazolin-8-yl)oxyhexanamide;
N-cyclopentylbutyl-N-(2-hydroxyethyl)-6-(2-oxo-1,2,3,5-tetrahydroimidazo[2,1-b]quinazolin-8-yl)oxyhexanamide;
($\pm$)-decahydroquinolinyl-6-(2-oxo-1,2,3,5-tetrahydroimidazo[2,1-b]quinazolin-8-yl)oxyhexanamide;
N-diphenylmethyl-N-methyl-6-(2-oxo-1,2,3,5-tetrahydroimidazo[2,1-b]quinazolin-8-yl)oxyhexanamide;
N-phenyl-N-(2-hydroxyethyl)-6-(2-oxo-1,2,3,5-tetrahydroimidazo[2,1-b]quinzolin-8-yl)oxyhexanamide;
N-phenyl-N-hexyl-6-(2-oxo-1,2,3,5-tetrahydroimidazo[2,1-b]quinazolin-8-yl)oxyhexanamide;
N-(4-chlorobenzyl)-N-(2-hydroxyethyl)-6-(2-oxo-1,2,3,5-tetrahydroimidazo[2,1-b]quinazolin-8-yl)oxyhexanamide;
N-cyclohexyl-N-(6-hydroxyhexyl)-6-(2-oxo-1,2,3,5-tetrahydroimidazo[2,1-b]quinazolin-8-yl)oxyhexanamide;
N-cyclohexyl-N-(2-hydroxyethyl)-6-(2-oxo-1,2,3,5-tetrahydroimidazo[2,1-b]quinazolin-9-yl)oxyhexanamide;
N-cyclopentyl-N-(2-hydroxyethyl)-6-(2-oxo-1,2,3,5-tetrahydroimidazo[2,1-b]quinazolin-9-yl)oxyhexanamide;
N-phenyl-N-methyl-6-(2-oxo-1,2,3,5-tetrahydroimidazo[2,1-b]quinazolin-9-yl)oxyhexanamide;
N-cyclohexylbutyl-N-(2-hydroxyethyl)-6-(2-oxo-1,2,3,5-tetrahydroimidazo[2,1-b]quinazolin-9-yl)oxyhexanamide;
N-cyclohexyl-N-methyl-6-(2-oxo-1,2,3,5-tetrahydroimidazo[2,1-b]quinazolin-9-yl)oxyhexanamide;
N-benzyl-N-methyl-6-(2-oxy-1,2,3,5-tetrahydroimidazo[2,1-b]quinazolin-9-yl)oxyhexanamide;
N-cyclopentyl-N-(2-hydroxyethyl)-6-(2-oxy-6-methyl-1,2,3,5-tetrahydroimidazo[2,1-b]quinazolin-9-yl)oxyhexanamide;
N-cyclohexyl-N-(6-hydroxyhexyl)-6-(2-oxo-1,2,3,5-tetrahydroimidazo[2,1-b]quinazolin-9-yl)oxyhexanamide;
N-phenyl-N-(2-hydroxyethyl)-6-(2-oxo-1,2,3,5-tetrahydroimidazo[2,1-b]quinazolin-9-yl)oxyhexanamide; and
($\pm$)-decahydroquinolinyl-N-methyl-4-(2-oxo-1,2,3,5-tetrahydroimidazo[2,1-b]quinazolin-9-yl)oxyhexanamide.

EXAMPLE 3

To a solution of N-cyclohexyl-N-methyl-4-(3-formyl-4-nitrophenyl)oxybutyramide (25 mmol), D-serine methyl ester hydrochloride (7.0 g, 50 mmol) and 3 Å molecular seives (5.0 g) in methanol (75 ml) was added D-serine methyl ester (20.6 g, 200 mmol). After allowing the solution to stir for 5 minutes at room temperature, sodium cyanoborohydride (0.95 g, 15 mmol) was added in one amount. The reaction mixture was allowed to stir at room temperature for 3–4 hours. The reaction solution was then filtered to remove precipitated solids and molecular sieves, and the methanol was removed by evaporation. The residue was dissolved in ethyl acetate (300 ml) and was washed with 2N sodium hydroxide (2×100 ml) in brine (2×100 ml). The organic extract was dried, filtered and evaporated to give a thick syrup. The thick syrupy residue was dissolved in absolute ethanol (100 ml) and hydrogenated over 10% Pd-C (1.0 g) until uptake of hydrogen ceased, approximately 4 hours. The catalyst was removed by filtration through a pad of Celite, and pad was washed clean with absolute ethanol (50 ml). The combined filtrates from the previous paragraph were treated with cyanogen bromide (3.20 g, 30 mmol), and the resulting solution maintained at a reflux for 16 hours. Upon cooling, the ethanol was removed, and the residue was dissolved in ethanol (100 ml) and treated with 6N sodium hydroxide (5 ml, 30 mmol) and stirred for 2 hours at room temperature. The product precipitated from this mixture and it was further purified by filtration and a water wash and dried, yielding N-cyclohexyl-N-methyl-4-(2-oxo-3-D-hydroxymethyl-1,2,3,5-tetrahydroimidazo[2,1-b]quinazolin-7-yl)oxybutyramide, m.p. 218°–219° C.

Proceeding in a like manner but substituting D-serine methyl ester with other appropriate optically active aminocarboxylic acid esters, there may be prepared the following exemplary optical isomers of Formula I:
N-cyclohexyl-N-methyl-4-(2-oxo-3-L-hydroxymethyl-1,2,3,5-tetrahydroimidazo[2,1-b]quinazolin-7-yl)oxybutyramide, m.p. 219°–220° C.;
N-cyclohexyl-N-methyl-4-(2-oxo-3-L-methyl-1,2,3,5-tetrahydroimidazo[2,1-b]quinazolin-7-yl)oxybutyramide, m.p. 119°–120° C.;
N-cyclohexyl-N-methyl-4-(2-oxo-3-D-methyl-1,2,3,5-tetrahydroimidazo[2,1-b]quinazolin-7-yl)oxybutyramide, m.p. 120°–121° C.;
N-cyclohexyl-N-methyl-4-(2-oxo-3-D-ethyl-1,2,3,5-tetrahydroimidazo[2,1-b]quinazolin-7-yl)oxybutyramide, m.p. 185°–186° C.;
N-cyclohexyl-N-methyl-4-(2-oxo-3-L-ethyl-1,2,3,5-tetrahydroimidazo[2,1-b]quinazolin-7-yl)oxybutyramide, m.p. 184°–185° C.;
N-cyclohexyl-N-methyl-4-(2-oxo-3-D-(1-hydroxyethyl)-1,2,3,5-tetrahydroimidazo[2,1-b]quinazolin-7-yl)oxybutyramide, m.p. 211°–212° C.;
N-cyclohexyl-N-methyl-4-(2-oxo-3-L-(1-hydroxyethyl)-1,2,3,5-tetrahydroimidazo[2,1-b]quinazolin-7-yl)oxybutyramide, m.p. 210°–211° C.;
N-cyclohexyl-N-methyl-4-(2-oxo-3-D-isopropyl-1,2,3,5-tetrahydroimidazo[2,1-b]quinazolin-7-yl)oxybutyramide, m.p. 178°–179° C.;
N-cyclohexyl-N-methyl-4-(2-oxo-3-L-isopropyl-1,2,3,5-tetrahydroimidazo[2,1-b]quinazolin-7-yl)oxybutyramide, m.p. 176°–177° C.;
N-cyclohexyl-N-methyl-4-(2-oxo-3-D-benzyl-1,2,3,5-tetrahydroimidazo[2,1-b]quinazolin-7-yl)oxybutyramide, m.p. 228°–229° C.;
N-cyclohexyl-N-methyl-4-(2-oxo-3-L-benzyl-1,2,3,5-tetrahydroimidazo[2,1-b]quinazolin-7-yl)oxybutyramide, m.p. 228°–229° C.;
N-cyclohexyl-N-methyl-4-(2-oxo-3-D-phenyl-1,2,3,5-tetrahydroimidazo[2,1-b]quinazolin-7-yl)oxybutyramide, m.p. 201°–202° C.;

N-cyclohexyl-N-methyl-4-(2-oxo-3-L-phenyl-1,2,3,5-tetrahydroimidazo[2,1-b]quinazolin-7-yl)oxybutyramide, m.p. 201°-202° C.

N-cyclohexyl-N-methyl-4-(2-oxo-3-D-acetoxymethyl-1,2,3,5-tetrahydroimidazo[2,1-b]quinazolin-7-yl)oxybutyramide;

N-cyclohexyl-N-methyl-4-(2-oxo-3-L-acetoxymethyl-1,2,3,5-tetrahydroimidazo[2,1-b]quinazolin-7-yl)oxybutyramide;

N-cyclohexyl-N-methyl-4-(2-oxo-3-D-carbamoylmethyl-1,2,3,5-tetrahydroimidazo[2,1-b]quinazolin-7-yl)oxybutyramide; and N-cyclohexyl-N-methyl-4-(2-oxo-3-L-carbamoylmethyl-1,2,3,5-tetrahydroimidazo[2,1-b]quinazolin-7-yl)oxybutyramide.

EXAMPLE 4

Preparation of N-cyclohexyl-N-methyl-4-(2,5-dioxo-1,2,3,5-tetrahydroimidazo[2,1-b]quinazolin-7-yl)oxybutyramide and related compounds.

To a suspension of 5-(N-cyclohexyl-N-methylbutyramid-4-yl)oxyanthranilic acid (0.05 g, 1.5 mmol) in ethanol (10 ml) was added an ethanolic solution of freshly prepared 2-methylthiohydantoin (3.4 mmol). The dark mixture was heated and maintained at reflux for 3 hours. The reaction mixture was then cooled, diluted with water and triturated to give N-cyclohexyl-N-methyl-4-(2,5-dioxo-1,2,3,5-tetrahydroimidazo[2,1-b]quinazolin-7-yl)oxybutyramide, m.p. 200°-202° C.

Proceeding in a similiar manner, but substituting the appropriate anthranilic acid from Preparation 9 for 5-(N-cyclohexyl-N-methylbutyramid-4-yl)oxyanthranilic acid there is prepared the following exemplary compounds:

N-cyclohexyl-N-(2-hydroxyethyl)-4-(2,5-dioxo-1,2,3,5-tetrahydroimidazo[2,1-b]quinazolin-7-yl-oxybutyramide;

N-cyclohexylmethyl-N-(2-hydroxyethyl)-4-(2,5-dioxo-1,2,3,5-tetrahydroimidazo[2,1-b]quinazolin-7-yl)oxybutyramide;

N-phenyl-N-methyl-4-(2,5-dioxo-1,2,3,5-tetrahydroimidazo[2,1-b]quinazolin-7-yl)oxybutyramide;

N-cyclohexylmethyl-N-(2-hydroxyethyl)-4-(2,5-dioxo-5-methyl-1,2,3,5-tetrahydroimidazo[2,1-b]quinazolin-7-yl)oxybutyramide;

N-phenyl-N-methyl-4-(2,5-dioxo-3-methyl-1,2,3,5-tetrahydroimidazo]2,1-b]quinazolin-7-yl)oxybutyramide;

N-cyclohexyl-N-(2-hydroxyethyl)-4-(2,5-dioxo-6-chloro-1,2,3,5-tetrahydroimidazo[2,1-b]quinazolin-7-yl)oxybutyramide;

N-cyclohexylmethyl-N-(2-hydroxyethyl)-4-(2,5-dioxo-3-ethyl-6-chloro-1,2,3,5-tetrahydroimidazo[2,1-b]quinazolin-7-yl)oxybutyramide;

N-cyclohexyl-N-(2-hydroxyethyl)-4-(2,5-dioxo-9-methyl-1,2,3,5-tetrahydroimidazo[2,1-b]quinazolin-7-yl)oxybutyramide;

N-cyclohexyl-N-methyl-4-(2,5-dioxo-9-chloro-1,2,3,5-tetrahydroimidazo[2,1-b]quinazolin-7-yl)oxybutyramide;

N-benzyl-N-methyl-4-(2,5-dioxo-1,2,3,5-tetrahydroimidazo[2,1-b]quinazolin-7-yl)oxybutyramide;

N,N-dibenzyl-4-(2,5-dioxo-1,2,3,5-tetrahydroimidazo[2,1-b]quinazolin-7-yl)oxybutyramide;

N,N-dicyclohexyl-4-(2,5-dioxo-1,2,3,5-tetrahydroimidazo[2,1-b]quinazolin-7-yl)oxybutyramide;

morpholinyl-4-(2,5-dioxo-1,2,3,5-tetrahydroimidazo[2,1-b]quinazolin-7-yl)oxybutyramide;

piperidinyl-4-(2,5-dioxo-1,2,3,5-tetrahydroimidazo[2,1-b]quinazolin-7-yl)oxybutyramide;

pyrrolidinyl-4-(2,5-dioxo-1,2,3,5-tetrahydroimidazo[2,1-b]quinazolin-7-yl)oxybutyramide;

N-cyclopentyl-N-(2-hydroxyethyl)-4-(2,5-dioxo-6-chloro-1,2,3,5-tetrahydroimidazo[2,1-b]quinazolin-7-yl)oxybutyramide;

N-cyclopentylmethyl-N-(2-hydroxyethyl)-4-(2,5-dioxo-1,2,3,5-tetrahydroimidazo[2,1-b]quinazolin-7-yl)oxybutyramide;

N-methylpiperazinyl-4-(2,5-dioxo-1,2,3,5-tetrahydroimidazo[2,1-b]quinazolin-7-yl)oxybutyramide;

tetrahydroquinolinyl-4-(2,5-dioxo-1,2,3,5-tetrahydroimidazo[2,1-b]quinazolin-7-yl)oxybutyramide;

tetrahydroisoquinolinyl-4-(2,5-dioxo-1,2,3,5-tetrahydroimidazo[2,1-b]quinazolin-7-yl)oxybutyramide;

indolinyl-4-(2,5-dioxo-1,2,3,5-tetrahydroimidazo[2,1-b]quinazolin-7-yl)oxybutyramide;

(±)-decahydroquinolinyl-4-(2,5-dioxo-1,2,3,5-tetrahydroimidazo[2,1-b]quinazolin-7-yl)oxybutyramide;

N-diphenylmethyl-N-methyl-4-(2,5-dioxo-1,2,3,5-tetrahydroimidazo[2,1-b]quinazolin-7-yl)oxybutyramide;

N,N-dimethyl-4-(2,5-dioxo-9-methyl-1,2,3,5-tetrahydroimidazo[2,1-b]quinazolin-7-yl)oxybutyramide;

N-methyl-N-n-hexyl-4-(2,5-dioxo-1,2,3,5-tetrahydroimidazo[2,1-b]quinazolin-7-yl)oxybutyramide;

N,N-di-n-hexyl-4-(2,5-dioxo-1,2,3,5-tetrahydroimidazo[2,1-b]quinazolin-7-yl)oxybutyramide;

N-n-hexyl-N-(2-hydroxyethyl)-4-(2,5-dioxo-1,2,3,5-tetrahydroimidazo-[2,1-b]quinazolin-7-yl)oxybutyramide;

N,N-di(2-hydroxyethyl)-4-(2,5-dioxo-1,2,3,5-tetrahydroimidazo[2,1-b]quinazolin-7-yl)oxybutyramide;

N-phenyl-N-(2-hydroxyethyl)-4-(2,5-dioxo-1,2,3,5-tetrahydroimidazo[2,1-b]quinazolin-7-yl)oxybutyramide;

N-phenyl-N-n-hexyl-4-(2,5-dioxo-1,2,3,5-tetrahydroimidazo[2,1-b]quinazolin-7-yl)oxybutyramide;

N-benzyl-N-methyl-4-(2,5-dioxo-1,2,3,5-tetrahydroimidazo[2,1-b]quinazolin-7-yl)oxybutyramide;

N-phenethyl-N-(2-hydroxyethyl)-4-(2,5-dioxo-1,2,3,5-tetra-hydroimidazo-[2,1-b]quinazolin-7-yl)oxybutyramide;

N-benzyl-N-(2-hydroxyethyl)-4-(2,5-dioxo-1,2,3,5-tetrahydroimidazo-[2,1-b]quinazolin-7-yl)oxybutyramide;

N-(4-chlorobenzyl)-N-methyl-4-(2,5-dioxo-1,2,3,5-tetrahydroimidazo-[2,1-b]quinazolin-7-yl)oxybutyramide;

N-(4-methoxybenzyl)-N-methyl-4-(2,5-dioxo-1,2,3,5-tetrahydroimidazo-[2,1-b]quinazolin-7-yl)oxybutyramide;

N-cyclohexyl-N-(6-hydroxyhexyl)-4-(2,5-dioxo-1,2,3,5-tetrahydroimidazo-[2,1-b]quinazolin-7-yl)oxybutyramide;

N-cyclohexyl-N-(2-hydroxyethyl)-4-(2,5-dioxo-1,2,3,5-tetrahydroimidazo[2,1-b]quinazolin-6-yl)oxybutyramide;

N-cyclohexyl-N-(2-hydroxyethyl)-4-(2,5-dioxo-1,2,3,5-tetrahydroimidazo[2,1-b]quinazolin-6-yl)oxybutyramide;

N-cyclohexylbutyl-N-(2-hydroxyethyl)-4-(2,5-dioxo-1,2,3,5-tetrahydroimidazo[2,1-b]quinazolin-6-yl)oxybutyramide;

N-phenyl-N-methyl-4-(2,5-dioxo-1,2,3,5-tetrahydroimidazo[2,1-b]quinazolin-6-yl)oxybutyramide;
N-cyclohexyl-N-(2-hydroxyethyl)-4-(2,5-dioxo-7-chloro-1,2,3,5-tetrahydroimidazo[2,1-b]quinazolin-6-yl)oxybutyramide;
N-cyclohexyl-N-(2-hydroxyethyl)-4-(2,5-dioxo-7-methyl-1,2,3,5-tetrahydroimidazo[2,1-b]quinazolin-6-yl)oxybutyramide;
N-cyclohexyl-N-methyl-4-(2,5-dioxo-9-chloro-1,2,3,5-tetra-hydroimidazo[2,1-b]quinazolin-6-yl)oxybutyramide;
N-cyclohexyl-N-methyl-4-(2,5-dioxo-1,2,3,5-tetrahydroimidazo[2,1-b]quinazolin-8-yl)oxybutyramide;
N-cyclohexyl-N-methyl-4-(2,5-dioxo-1,2,3,5-tetrahydroimidazo[2,1-b]quinazolin-8-yl)oxybutyramide;
N-cyclohexyl-N-methyl-4-(2,5-dioxo-1,2,3,5-tetrahydroimidazo[2,1-b]quinazolin-8-yl)oxybutyramide;
N-cyclohexyl-N-(2-hydroxyethyl)-4-(2,5-dioxo-1,2,3,5-tetrahydroimidazo[2,1-b]quinazolin-8-yl)oxybutyramide;
N-cyclohexyl-N-(2-hydroxyethyl)-4-(2,5-dioxo-1,2,3,5-tetrahydroimidazo[2,1-b]quinazolin-9-yl)oxybutyramide;
N-cyclohexylmethyl-N-(2-hydroxyethyl)-4-(2,5-dioxo-1,2,3,5-tetrahydroimidazo[2,1-b]quinazolin-8-yl)oxybutyramide;
N-cyclohexylbutyl-N-(2-hydroxyethyl)-4-(2,5-dioxo-1,2,3,5-tetrahydroimidazo[2,1-b]quinazolin-8-yl)oxybutyramide;
N-cyclohexylmethyl-N-(2-hydroxyethyl)-4-(2,5-dioxo-1,2,3,5-tetrahydroimidazo[2,1-b]quinazolin-9-yl)oxybutyramide;
N-n-hexyl-N-(2-hydroxyethyl)-4-(2,5-dioxo-1,2,3,5-tetrahydroimidazo[2,1-b]quinazolin-8-yl)oxybutyramide;
N-cyclohexylmethyl-N-(2-hydroxyethyl)-4-(2,5-dioxo-1,2,3,5-tetrahydroimidazo[2,1-b]quinazolin-9-yl)oxybutyramide;
N-cyclohexylbutyl-N-(2-hydroxyethyl)-4-(2,5-dioxo-1,2,3,5-tetrahydroimidazo[2,1-b]quinazolin-9-yl)oxybutyramide;
N-cyclohexylbutyl-N-(6-hydroxyhexyl)-4-(2,5-dioxo-1,2,3,5-tetrahydroimidazo[2,1-b]quinazolin-9-yl)oxybutyramide;
N-cyclopentyl-N-(2-hydroxyethyl)-7-(2,5-dioxo-1,2,3,5-tetrahydroimidazo[2,1-b]quinazolin-7-yl)oxyheptanamide;
N-cyclohexyl-N-(2-hydroxyethyl)-7-(2,5-dioxo-1,2,3,5-tetrahydroimidazo[2,1-b]quinazolin-7-yl)oxyheptanamide;
N-cyclohexyl-N-methyl-7-(2,5-dioxo-1,2,3,5-tetrahydroimidazo[2,1-b]quinazolin-7-yl)oxyheptanamide;
N-cyclopentyl-N-methyl-7-(2,5-dioxo-1,2,3,5-tetrahydroimidazo[2,1-b]quinazolin-7-yl)oxyheptanamide;
N-cyclohexyl-N-(2-hydroxyethyl)-7-(2,5-dioxo-1,2,3,5-tetrahydroimidazo[2,1-b]quinazolin-6-yl)oxyheptanamide;
N-cyclohexyl-N-(2-hydroxyethyl)-7-(2,5-dioxo-1,2,3,5-tetrahydroimidazo[2,1-b]quinazolin-8-yl)oxyheptanamide;
N-cyclohexyl-N-(2-hydroxyethyl)-7-(2,5-dioxo-1,2,3,5-tetrahydroimidazo[2,1-b]quinazolin-9-yl)oxyheptanamide;
(±)-decahydroquinolinyl-7-(2,5-dioxo-1,2,3,5-tetrahydroimidazo[2,1-b]quinazolin-7-yl)oxyheptanamide;
N-cyclopentyl-N-(2-hydroxyethyl)-5-(2,5-dioxo-1,2,3,5-tetrahydroimidazo[2,1-b]quinazolin-7-yl)oxypentanamide;
N-cyclopentyl-N-(2-hydroxyethyl)-5-(2,5-dioxo-1,2,3,5-tetrahydroimidazo[2,1-b]quinazolin-7-yl)oxypentanamide;
N-cyclohexylbutyl-N-(2-hydroxyethyl)-5-(2,5-dioxo-1,2,3,5-tetrahydroimidazo[2,1-b]quinazolin-7-yl)oxypentanamide;
N-cyclohexyl-N-methyl-5-(2,5-dioxo-1,2,3,5-tetrahydroimidazo[2,1-b]quinazolin-7-yl)oxypentanamide;
N-cyclopentyl-N-methyl-5-(2,5-dioxo-1,2,3,5-tetrahydroimidazo[2,1-b]quinazolin-7-yl)oxypentanamide;
N-cyclohexyl-N-(2-hydroxyethyl)-5-(2,5-dioxo-1,2,3,5-tetrahydroimidazo[2,1-b]quinazolin-6-yl)oxypentanamide;
N-cyclopentyl-N-methyl-5-(2,5-dioxo-6-methyl-1,2,3,5-tetrahydroimidazo[2,1-b]quinazolin-7-yl)oxypentanamide;
N-cyclohexyl-N-(2-hydroxyethyl)-5-(2,5-dioxo-1,2,3,5-tetrahydroimidazo[2,1-b]quinazolin-8-yl)oxypentanamide;
N-cyclohexyl-N-(2-hydroxyethyl)-5-(2,5-dioxo-6-chloro-1,2,3,5-tetrahydroimidazo[2,1-b]quinazolin-8-yl)oxypentanamide;
N-cyclohexyl-N-(2-hydroxyethyl)-5-(2,5-dioxo-1,2,3,5-tetrahydroimidazo[2,1-b]quinazolin-9-yl)oxypentanamide;
(±)-decahydroquinolinyl-5-(2,5-dioxo-1,2,3,5-tetrahydroimidazo[2,1-b]quinazolin-7-yl)oxypentanamide;
(±)-decahydroquinolinyl-5-(2,5-dioxo-1,2,3,5-tetrahydroimidazo[2,1-b]quinazolin-6-yl)-oxypentanamide;
(±)-decahydroquinolinyl-5-(2,5-dioxo-1,2,3,5-tetrahydroimidazo[2,1-b]quinazolin-8-yl)oxypentanamide;
N-cyclopentyl-N-(2-hydroxyethyl)-6-(2,5-dioxo-1,2,3,5-tetrahydroimidazo[2,1-b]quinazolin-7-yl)oxyhexanamide;
N-pentyl-N-(2-hydroxyethyl)-6-(2,5-dioxo-1,2,3,5-tetrahydroimidazo[2,1-b]quinazolin-7-yl)oxyhexanamide;
N-cyclohexylbutyl-N-(2-hydroxyethyl)-6-(2,5-dioxo-1,2,3,5-tetrahydroimidazo[2,1-b]quinazolin-7-yl)-oxyhexanamide;
N-cyclohexyl-N-methyl-6-(2,5-dioxo-1,2,3,5-tetrahydroimidazo[2,1-b]quinazolin-7-yl)oxyhexanamide;
N-cyclopentylmethyl-N-methyl-6-(2,5-dioxo-1,2,3,5-tetrahydroimidazo[2,1-b]quinazolin-7-yl)oxyhexanamide;
N-cyclohexyl-N-(2-hydroxyethyl)-6-(2,5-dioxo-1,2,3,5-tetrahydroimidazo[2,1-b]quinazolin-6-yl)oxyhexanamide;
N-cyclopentyl-N-methyl-6-(2,5-dioxo-6-methyl-1,2,3,5-tetrahydroimidazo[2,1-b]quinazolin-7-yl)oxyhexanamide;
N-cyclohexyl-N-(2-hydroxyethyl)-6-(2,5-dioxo-1,2,3,5-tetrahydroimidazo[2,1-b]quinazolin-8-yl)oxyhexanamide;
N-cyclohexylbutyl-N-(2-hydroxyethyl)-6-(2,5-dioxo-6-chloro-1,2,3,5-tetrahydroimidazo[2,1-b]quinazolin-8-yl)oxyhexanamide;
N-phenyl-N-(2-hydroxyethyl)-6-(2,5-dioxo-1,2,3,5-tetrahydroimidazo[2,1-b]quinazolin-7-yl)oxyhexanamide;
(±)-decahydroquinolinyl-6-(2,5-dioxo-1,2,3,5-tetrahydroimidazo[2,1-b]quinazolin-7-yl)oxyhexanamide;
(±)-decahydroquinolinyl-6-(2,5-dioxo-1,2,3,5-tetrahydroimidazo[2,1-b]quinazolin-6-yl)oxyhexanamide; and
(±)-decahydroquinolinyl-6-(2,5-dioxo-1,2,3,5-tetrahydroimidazo[2,1-b]quinazolin-8-yl)oxyhexanamide.

EXAMPLE 5

The formation of N-cyclohexyl-N-(acetoxyethyl)-4-(2-oxo-1,2,3,5-tetrahydroimidazo[2,1-b]quinazolin-7-yl)oxybutyramide and analogues thereof is carried out as follows.

A solution of N-cyclohexyl-N-(2-hydroxyethyl)-4-(oxo-1,2,3,5-tetrahydroimadizo[2,1-b]quinazolin-7-yl)oxybutyramide (2.07 mg) in acetic anhydride and pyridine (1 ml each) was treated with N,N-dimethylaminopyridine (6 mg), and was stirred at room temperature for 1 hour. The solution was poured into water, and the resulting pyrcipitate was collected and dried to yield the captioned compound, m.p. 164°–166° C.

Proceeding in a similar manner, but substituting the appropriate N-hydroxyalkyl compound from Examples 2 for N-cyclohexyl-N-(acetoxyethyl)-4-(2-oxo-1,2,3,5-tetrahydroimidazo[2,1-b]quinazolin-7-yl)oxybutyramide, all N-hydroxyalkyl-substituted compounds may be converted to their corresponding acylate, exemplified by the following compounds:

N-cyclohexyl-N-(acetoxyethyl)-4-(2-oxo-1,2,3,5-tetrahydroimidazo[2,1-b]quinazolin-7-yl)oxybutyramide, m.p. 164°–166° C.;
N-cyclohexyl-N-(isopropionyloxyethyl)-4-(2-oxo-1,2,3,5-tetrahydroimidazo[2,1-b]quinazolin-7-yl)oxybutyramide, m.p. 154°–155° C.;
N-cyclohexyl-N-(butyryloxyethyl)-4-(2-oxo-1,2,3,5-tetrahydroimidazo[2,1-b]quinazolin-7-yl)oxybutyramide, m.p. 152°–153° C.;
N-cyclohexyl-N-(4-acetoxybutyl)-4-(2-oxo-1,2,3,5-tetrahydroimidazo[2,1-b]quinazolin-7-yl)oxybutyramide;
N-cyclopentyl-N-(acetoxyethyl)-4-(2-oxo-1,2,3,5-tetrahydroimidazo[2,1-b]quinazolin-7-yl)oxybutyramide;
N-cyclohexyl-N-(6-acetoxyhexyl)-4-(2-oxo-1,2,3,5-tetrahydroimidazo[2,1-b]quinazolin-7-yl)oxybutyramide;
N-cyclohexyl-N-(formyloxyethyl)-4-(2-oxo-1,2,3,5-tetrahydroimidazo[2,1-b]quinazolin-7-yl)oxybutyramide;
N-cyclohexyl-N-(hexanyloxyethyl)-4-(2-oxo-1,2,3,5-tetrahydroimidazo[2,1-b]quinazolin-7-yl)oxybutyramide;
N-cyclohexyl-N-(6-benzoyloxyhexyl)-4-(2-oxo-1,2,3,5-tetrahydroimidazo[2,1-b]quinazolin-7-yl)oxybutyramide;
N-cyclopentyl-N-(benzoyloxyethyl)-4-(2-oxo-1,2,3,5-tetrahydroimidazo[2,1-b]quinazolin-7-yl)oxybutyramide, m.p. 94°–95° C.;
N-benzyl-N-(acetoxyethyl)-4-(2-oxo-1,2,3,5-tetrahydroimidazo[2,1-b]quinazolin-7-yl)oxybutyramide;
N-cyclohexylbutyl-N-(formyloxyethyl)-4-(2-oxo-1,2,3,5-tetrahydroimidazo[2,1-b]quinazolin-7-yl)oxybutyramide;
N-cyclopentylpropyl-N-(acetoxyethyl)-4-(2-oxo-1,2,3,5-tetrahydroimidazo[2,1-b]quinazolin-7-yl)oxybutyramide;
N-hexyl-N-(3-acetoxypropyl)-4-(2-oxo-1,2,3,5-tetrahydroimidazo[2,1-b]quinazolin-7-yl)oxybutyramide;
N-phenyl-N-(acetoxyethyl)-4-(2-oxo-1,2,3,5-tetrahydroimidazo[2,1-b]quinazolin-7-yl)oxybutyramide;
N-cyclohexyl-N-(acetoxyethyl)-5-(2-oxo-1,2,3,5-tetrahydroimidazo[2,1-b]quinazolin-7-yl)oxypentanamide;
N-cyclohexyl-N-(acetoxyethyl)-5-(2-oxo-1,2,3,5-tetrahydroimidazo[2,1-b]quinazolin-7-yl)oxypentanamide;
N-cyclohexyl-N-(6-acetoxyhexyl)-5-(2-oxo-1,2,3,5-tetrahydroimidazo[2,1-b]quinazolin-7-yl)oxypentanamide;
N-cyclopentyl-N-(acetoxyethyl)-5-(2-oxo-1,2,3,5-tetrahydroimidazo[2,1-b]quinazolin-7-yl)oxypentanamide;
N-cyclohexyl-N-(6-benzoyloxyhexyl)-5-(2-oxo-1,2,3,5-tetrahydroimidazo[2,1-b]quinazolin-7-yl)oxypentanamide;
N-cyclohexyl-N-(butyloxyethyl)-5-(2-oxo-1,2,3,5-tetrahydroimidazo[2,1-b]quinazolin-7-yl)oxypentanamide;
N-cyclohexyl-N-(3-acetoxypropyl)-5-(2-oxo-1,2,3,5-tetrahydroimidazo[2,1-b]quinazolin-7-yl)oxypentanamide;
N-cyclopentyl-N-(benzoyloxyethyl)-5-(2-oxo-1,2,3,5-tetrahydroimidazo[2,1-b]quinazolin-7-yl)oxypentanamide;
N-benzyl-N-(acetoxyethyl)-5-(2-oxo-1,2,3,5-tetrahydroimidazo[2,1-b]quinazolin-7-yl)oxypentanamide;
N-cyclohexylbutyl-N-(acetoxyethyl)-5-(2-oxo-1,2,3,5-tetrahydroimidazo[2,1-b]quinazolin-7-yl)oxypentanamide;
N-cyclopentylpropyl-N-(acetoxyethyl)-5-(2-oxo-1,2,3,5-tetrahydroimidazo[2,1-b]quinazolin-7-yl)oxypentanamide;
N-hexyl-N-(3-acetoxypropyl)-5-(2-oxo-1,2,3,5-tetrahydroimidazo[2,1-b]quinazolin-7-yl)oxypentanamide;
N-phenyl-N-(benzolyoxyethyl)-5-(2oxo-1,2,3,5-tetrahydroimidazo[2,1-b]quinazolin-7-yl)oxypentanamide;
N-cyclohexyl-N-(acetoxyethyl)-7-(2-oxo-1,2,3,5-tetrahydroimidazo[2,1-b]quinazolin-7-yl)oxyheptanamide;
N-cyclohexyl-N-(3-acetoxypropyl)-7-(2-oxo-1,2,3,5-tetrahydroimidazo[2,1-b]quinazolin-7-yl)oxyheptanamide;
N-cyclohexyl-N-(6-acetoxyhexyl)-7-(2-oxo-1,2,3,5-tetrahydroimidazo[2,1-b]quinazolin-7-yl)oxyheptanamide;
N-cyclopentyl-N-(acetoxyethyl)-7-(2-oxo-1,2,3,5-tetrahydroimidazo[2,1-b]quinazolin-7-yl)oxyheptanamide;
N-cyclohexyl-N-(6-benzolyoxyhexyl)-7-(2oxo-1,2,3,5-tetrahydroimidazo[2,1-]quinazolin-7-yl)oxyheptanamide;
N-cyclohexylmethyl-N-(acetoxyethyl)-7-(2-oxo-1,2,3,5-tetrahydroimidazo[2,1-b]quinazolin-7-yl)oxyheptanamide;
N-cyclopentyl-N-(acetoxyethyl)-7-(2-oxo-1,2,3,5-tetrahydroimidazo[2,1-b]quinazolin-7-yl)oxyheptanamide;
N-benzyl-N-(acetoxyethyl)-7-(2oxo-1,2,3,5-tetrahydroimidazo[2,1-b]quinazolin-7-yl)oxyheptanamide;
N-cyclohexylbutyl-N-(3-acetoxypropyl)-7-(2-oxo-1,2,3,5-tetrahydroimidazo[2,1-b]quinazolin-7-yl)oxyheptanamide;
N-cyclopentylethyl-N-(acetoxyethyl)-7-(2-oxo-1,2,3,5-tetrahydroimidazo[2,1-b]quinazolin-7-yl)oxyheptanamide;
N-hexyl-N-(acetoxypropyl)-7-(2-oxo-1,2,3,5-tetrahydroimidazo[2,1-b]quinazolin-7-yl)oxyheptanamide;
N-phenyl-N-(acetoxyethyl)-7-(2-oxo-1,2,3,5-tetrahydroimidazo[2,1-b]quinazolin-7-yl)oxyheptanamide;
N-cyclohexyl-N-(acetoxyethyl)-1-(2-oxo-1,2,3,5-tetrahydroimidazo[2,1-b]quinazolin-7-yl)oxyacetamide;

N-cyclohexyl-N-(6-acetoxyhexyl)-1-(2-oxo-1,2,3,5-tetrahydroimidazo[2,1-b]quinazolin-7-yl)oxyacetamide;
N-cyclohexyl-N-(benzolyoxyethyl)-1-(2-oxo-1,2,3,5-tetrahydroimidazo[2,1-b]quinazolin-7-yl)oxyacetamide;
N-cyclopentyl-N-(acetoxyethyl)-1-(2-oxo-1,2,3,5-tetrahydroimidazo[2,1-b]quinazolin-7-yl)oxyacetamide;
N-cyclohexylmethyl-N-(acetoxyhexyl)-1-(2-oxo-1,2,3,5-tetrahydroimidazo[2,1-b]quinazolin-7-yl)oxyacetamide;
N-cyclohexyl-N-(6-benzoyloxyhexyl)-6-(2-oxo-1,2,3,5-tetrahydroimidazo[2,1-b]quinazolin-7-yl)oxyhexanamide;
N-cyclopentyl-N-(acetoxyethyl)-6-(2-oxo-1,2,3,5-tetrahydroimidazo[2,1-b]quinazolin-7-yl)oxyhexanamide;
N-hexyl-N-(acetoxyethyl)-6-(2-oxo-1,2,3,5-tetrahydroimidazo[2,1-b]quinazolin-7-yl)oxyhexanamide; and
N-cyclohexyl-N-(acetoxypropyl)-6-(2-oxo-1,2,3,5-tetrahydroimidazo[2,1-b]quinazolin-7-yl)oxyhexanamide.

EXAMPLE 6

N-Cyclohexyl-N-methyl-4-(2-oxo,1,2,3,5-tetrahydroimidazo[2,1-b]quinazolin-7-yl)oxybutyramide To a solution of 4-(2-oxo-1,2,3,5-tetrahydroimadazo[2,1-b]quinazolin-7-yl)oxybutyric acid (3.44 g) and 1-hydroxybenzotriazole (1.5 g) in 25 ml dry dimethylformamide was added diisopropylcarbodiimide (1.39 g). After one hour at room temperature, a solution of N-methylcyclohexylamine (1.56 ml) and 1.32 ml of N-methylmorpholine in 10 ml of dry dimethylformamide was added. The resulting solution was stirred overnight at room temperature and was then diluted with water. The resulting precipitate was collected and dried over phosphorous pentoxide to give N-cyclohexyl-N-methyl-4-(2-oxo-1,2,3,5-tetrahydroimadazo[2,1-b]quinazolin-7-yl)oxybutyramide.

Proceeding in a similiar manner, all oxyalkyl acids prepared as per Preparation 10 may be converted to their corresponding amide.

EXAMPLE 7

Ethylene glycol (50 ml) was saturated with ammonia gas at 0° C., and to it was added the ethyl ester described in Preparation 9 (3.2 g). The suspension was heated in a steel pressure apparatus for 3 days at 200° C. Upon cooling, the precipitate was collected by filtration, washed with ethanol and dried to yield the unsubstituted (2-oxo-1,2,3,5-tetrahydroimidazo[2,1-b]quinazolin-7-yl)oxybutyramide, m.p. 280°–282° C.

By using similar conditions with other primary amines, the corresponding primary amides can be prepared:
N-cyclohexyl-4-(2-oxo-1,2,3,5-tetrahydroimidazo[2,1-b]quinazolin-7-yl)oxybutyramide, m.p. 255°–256° C.;
N-methyl-4-(2-oxo-1,2,3,5-tetrahydroimidazo[2,1-b]quinazolin-7-yl)oxybutyramide; and
N-ethyl-4-(2-oxo-1,2,3,5-tetrahydroimidazo[2,1-b]quinazolin-7-yl)oxybutyramide.

EXAMPLE 8

Into a solution of the ethyl ester (3.2 g, 10 mmol) prepared from Preparation 9 and tetra-N-butylammonium bromide (6.44 g, 20 mmol) in DMF (100 ml) was added aqueous KOH (1.5 g in 5 ml H₂O), stirred overnight at room temperature. Molecular sieves (3A, 25 g) were added, and the mixture was left to stand 3 days. N-methylcyclohexylamine (2.6 ml, 20 mmol) and bis(o-nitrophenyl)phenylphosphonate (10 g, 25 mmol) were added, and the mixture was shaken for 24 hours. The mixture was filtered through Celite, and the DMF was evaporated at high vacuum. The residue was triturated with 5% aqueous ammonium hydroxide and ethanol (1:1) to give a precipitate, collected by filtration, washed with ethanol and dried to give N-cyclohexyl-N-methyl-4-(2-oxo-1,2,3,5-tetrahydroimidazo[2,1-b]quinazolin-7-yl)oxybutyramide, m.p. 243°–244° C.

EXAMPLE 9

The compounds of Formula I wherein $R_4$ is hydrogen are converted to those wherein $R_4$=alkyl of 1 to 6 carbon atoms, benzyl or hydroxyl lower alkyl by the following procedure.

To a solution of N-cyclohexyl-N-methyl-4-(2-oxo-1,2,3,5-tetrahydroimadazo[2,1-b]quinazolin-7-yl)oxybutyramide in dry dimethylformamide was added sodium hydride (1.05 equivalents). The mixture was stirred at 60° C. for 30 minutes to give a homogeneous solution. 1-bromobutane (1.1 equivalents) was added via a syringe after which the mixture was stirred at 60° C. for 2 hours. The solvent was evaporated and the residue taken up in ethyl acetate which was washed with saturated brine, dried and filtered. Evaporation of the solvent afforded N-cyclohexyl-N-methyl-4-(1-butyl-2-oxo-1,2,3,5-tetrahydroimadazo[2,1-b]quinazolin-7-yl)oxybutyramide.

EXAMPLE 10

Conversion of Free Base to Salt

A two-fold stoichiometric excess of 3% hydrogen chloride in methanol is added to a solution of 1.0 g. of N-cyclohexyl-N-methyl-4-(2-oxo-1,2,3,5-tetrahydroimidazo[2,1-b]quinazolin-7-yl)oxybutyramide in 20 ml methanol. Diethyl ether is added until precipitation is complete. The product is filtered, washed with ether, air dried and recrystallized to give N-cyclohexyl-N-methyl-4-(2-oxo-1,2,3,5-tetrahydroimidazo[2,1-b]quinazolin-7-yl)oxybutyramide hydrochloride, m.p. 232°–234° C.

In a similar manner, all compounds of Formula I in free base form may be converted to the acid addition salt by treatment with hydrogen chloride or another pharmaceutically acceptable acid addition salt-forming acid such as exemplified herein earlier.

EXAMPLE 11

Conversion of Salt to Free Base 1.0 g of N-cyclohexyl-N-methyl-4-(2-oxo-1,2,3,5-tetrahydroimidazo[2,1-b]quinazolin-7-yl)oxybutyramide HCl suspended in 50 ml of ether is stirred with a two-fold stoichiometric excess of dilute aqueous potassium carbonate solution until the salt is completely dissolved. The organic layer is then separated, washed twice with water, dried over magnesium sulfate and evaporated to yield N-cyclohexyl-N-methyl-4-(2-oxo-1,2,3,5-tetrahydroimidazo[2,1-b]quinazolin-7-yl)oxybutyramide as the free base.

EXAMPLE 12

Direct interchange of acid addition salts

N,N-dibenzyl-4-(2-oxo-1,2,3,5-tetrahydroimidazo[2,1-b]quinazolin-7-yl)oxybutyramide acetate (1.0 g) is dissolved in 50 ml water containing a stoichiometric equivalent of sulfuric acid, and the solution evaporated to dryness. The product is suspended in ethanol and filtered, air dried and recrystallized from methanol/acetone to yield N,N-dibenzyl-4-(2-oxo-1,2,3,5-tetrahydroimidazo[2,1-b]quinazolin-7-yl)oxybutyramide sulfate.

EXAMPLE 13

Compounds of the present invention, either the free base of a pharmaceutically acceptable acid addition salt, may be orally administered to a subject as a tablet. While the active ingredient may comprise anywhere between 5 and 90 percent of the formulation that percentage preferably will be an amount which will cause to be delivered to the subject, the active ingredient in an amount of between 20 mg and 100 mg per tablet. Following is a representative tablet formulation in which the active ingredient is N-cyclehexyl-N-methyl-4-(2-oxo-1,2,3,5-tetrahydroimidazo[2,1-b]quinazolin-7-yl)oxybutyramide. However, the formulation profile given below may be used to formulate a tablet for any of the compounds represented by Formula I.

| Ingredients | Quantity per tablet, mgs. |
|---|---|
| Active ingredient | 25 |
| cornstarch | 20 |
| lactose, spray-dried | 153 |
| magnesium stearate | 2 |

The above ingredients are thoroughly mixed and pressed into single scored tablets.

EXAMPLE 14

An alternative oral dosage form is to fill hard shell gelatin capsules with a powder containing the active ingredient in the desired amount. Using the active ingredient mentioned in Example 6 above, the acid addition salts, or any other compound according to Formula I there may be prepared an exemplary hard shell gelatin capsule formulation using the following ingredients

| Ingredients | Quantity per tablet, mgs. |
|---|---|
| Active ingredient | 100 |
| lactose, spray-dried | 148 |
| magnesium stearate | 2 |

The above ingredients are mixed and introduced into a hard-shell gelatin capsule.

EXAMPLE 15

Alternatively, compounds of the present invention may be prepared as a suspension for oral administration. Any of the compounds of Formula I, either in freelance form or as the acid addition salt, may be used in this formulation.

An oral suspension is prepared having the following composition:

| Ingredients | |
|---|---|
| Active ingredient | 0.1 g |
| fumaric acid | 0.5 g |
| sodium chloride | 2.0 g |
| methyl paraben | 0.1 g |
| granulated sugar | 25.5 g |
| sorbitol (70% solution) | 12.85 g |
| Veegum K (Vanderbilt Co.) | 1.0 g |
| flavoring | 0.035 ml |
| colorings | 0.5 mg |
| distilled water | q.s. to 100 ml |

EXAMPLE 16

Inotropic Activity

Mongrel dogs were anesthetized i.v. with 35 mg/Kg sodium pentobarbital and supplemented as needed. Blood pressure was measured with a Statham pressure transducer via a cannula inserted from a femoral artery into the abdominal aorta. Heart rate was recorded by a cardiotachometer from a lead II electrocardiogram. Right ventricular contractile force was recorded from a Walton-Brodie strain gauge sutured to the right ventricle following a midsternal thoracotomy. A Harvard respirator was used to ventilate the dogs with room air through an endotracheal tube. The dog was bilaterally vagotomized. Following a midline laparotomy, a cannula was sutured into the duodenum for intraduodenal administration of test compound. A femoral vein was cannulated for administration of isoproterenol. All data were recorded on a Beckman R611 Dynograph.

To assess the responsiveness of each dog, isoproterenol was given i.v. at half-log interval doses from 0.007 to 2.1 or 6.67 µg/Kg. The test compound was then administered intraduodenally, usually at a low dose of 2 mg/Kg and subsequently at higher doses of 6.32 and/or 20 mg/Kg, if necessary. In a few instances, some compounds administered intraduodenally at dose levels from 0.316 to 3.16 mg/Kg.

The test results are summarized in the following Table:

TABLE II

| | | Peak Effects as % of Max. Isoproterenol | | |
|---|---|---|---|---|
| Compound | dose (mg/kg) | Rt. Ventricular Contractile Force | Heart Rate | Blood Pressure |
| N—cyclohexyl-N—methyl-4-(2-oxo-1,2,3,5-tetrahydroimidazo-[2,1-b]quinazolin-7-yl]-oxybutyramide | 2 | 48 | 30 | 25 |
| | 6.23 | 44 | 40 | 96 |
| N—cyclohexyl-N—methyl-4-(2-oxo-3-L-methyl-1,2,3,5-tetrahydroimidazo-[2,1-b]quinazolin-7-yl) oxybutryamide | 0.316 | 23 | 11 | 17 |
| | 1.0 | 69 | 44 | 54 |
| | 3.16 | 55 | 58 | 94 |
| | 0.1 (i.v.) | 32 | 55 | 97 |
| N—cyclohexyl-N—methyl-4-(2-oxo-3-D-methyl-1,2,3,5-tetrahydro imidazo[2,1-b]quina-zolin-7-yl)oxybutyramide | 0.316 | 18 | 18 | 13 |
| | 1.0 | 50 | 48 | 49 |
| | 3.16 | 53 | 72 | 82 |
| | 0.1 (i.v.) | 43 | 73 | 82 |

What is claimed is:

1. A method of treating heart failure by stimulating suppressed heart activity which occurs during heart failure which method comprises administering a therapeutically effective amount of a compound of formula I alone or in admixture with a pharmaceutically acceptable excipient wherein formula I is

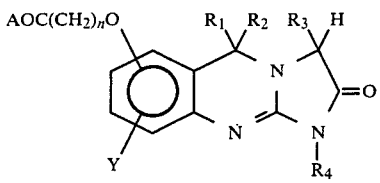

(I)

and the pharmaceutically acceptable acid addition salts thereof wherein n is an integer of 1 to 6;

$R_1$ is hydrogen or alkyl of 1 to 4 carbon;

$R_2$ is hydrogen or $R_1$ and $R_2$ combined are oxo;

$R_3$ is hydrogen, alkyl of 1 to 6 carbons, phenyl, benzyl, hydroxy lower alkyl and its acylates, carbamoyl alkyl, or carboxyalkyl;

$R_4$ is hydrogen, alkyl of 1 to 6 carbons, benzyl, or hydroxy lower alkyl;

Y is hydrogen, alkyl of 1 to 4 carbon atoms, halo or lower alkoxy;

A is an amide forming group wherein the nitrogen substituents are: hydrogen; alkyl of 1 to 6 carbon atoms; hydroxyalkyl of 1 to 6 carbon atoms and its aliphatic acylates of 1 to 6 carbon atoms or aryl acylates of 7 to 12 carbon atoms; cycloalkyl of 3 to 8 carbon atoms or cycloalkyl lower alkyl of 4 to 12 carbon atoms wherein the cycloalkyl ring is unsubstituted or substituted with a lower alkyl, lower alkoxy, —OH, —OCOR$_5$, halo, —NH$_2$, —N(R$_5$)$_2$, —NHCOR$_5$, —COOH, or —COO(R$_5$) group wherein R$_5$ is lower alkyl; phenyl or phenyl lower alkyl wherein phenyl is unsubstituted or substituted with 1 or more lower alkyl, halo or lower alkoxy groups or an —NH$_2$, —N(R$_5$)$_2$, —NHCOR$_5$, —COOH, or —COOR$_5$ group wherein R$_5$ is lower alkyl; morpholinyl; piperidinyl; perhexylenyl; N-loweralkylpiperazinyl; pyrrolidinyl; tetrahydroquinolinyl; tetrahydroisoquinolinyl; (±)-decahydroquinolinyl or indolinyl and the pharmaceutically acceptable salts thereof.

2. The method of claim 1 comprising a compound wherein n is 3 or 4, $R_1$, $R_2$ and $R_4$ are hydrogen, and $R_3$ is hydrogen, alkyl of 1 to 6 carbon atoms, phenyl, benzyl, hydroxy lower alkyl and its acylates or carbamoyl alkylates and the pharmaceutically acceptable salts thereof.

3. The method of claim 1 comprising a compound wherein n is 3 or 4; $R_1$, $R_2$ and $R_3$ are hydrogen; $R_4$ is hydrogen or methyl; and A is an amide wherein the nitrogen is substituted with alkyl of 1 to 6 carbon atoms, hydroxyalkyl of 1 to 6 carbon atoms and its aliphatic acylates of 1 to 6 carbon atoms or aryl acylates of 7 to 12 carbon atoms, cycloalkyl of 3 to 8 carbon atoms, cycloalkyl lower alkyl of 4 to 12 carbon atoms, phenyl or phenyl lower alkyl unsubstituted or substituted with 1 or more lower alkyl, halo or lower alkoxy groups; perhexylenyl; (±)-decahydroquinolinyl; morpholinyl; piperidinyl; pyrrolindinyl; tetrahydroquinolinyl; tetrahydroisoquinolinyl or indolinyl and the pharmaceutically acceptable salts thereof.

4. The method of claim 3 wherein the compound is N-cyclohexyl-N-methyl-4-(2-oxo-1,2,3,5-tetrahydroimidazo[2,1-b]quinazolin-7-yl)oxybutyramide and the pharmaceutically acceptable salts thereof.

5. The method of claim 3 wherein the compound is N-cyclohexyl-N-methyl-4-(2-oxo-L-methyl-1,2,3,5-tetra-hydroimidazo[2,1-b]quinazolin-7-yl)oxybutyramide and the pharmaceutically acceptable salts thereof.

6. The method of claim 3 wherein the compound is N-cyclohexyl-N-methyl-4-(2-oxo-D-methyl-1,2,3,5-tetrahydroimidazo[2,1-b]quinazolin-7-yl)oxybutyramide.

* * * * *